US007741286B2

(12) United States Patent
Bridon et al.

(10) Patent No.: US 7,741,286 B2
(45) Date of Patent: Jun. 22, 2010

(54) LONG LASTING ANTI-ANGIOGENIC PEPTIDES

(75) Inventors: Dominique P. Bridon, San Francisco, CA (US); Michele Rasamoelisolo, Montreal (CA); Karen Thibaudeau, Montreal (CA); Xicai Huang, Kirkland (CA); Richard Beliveau, Verdun (CA)

(73) Assignee: ConjuChem Biotechnologies Inc., Montreal (CA)

( * ) Notice: Subject to any disclaimer, the term of this patent is extended or adjusted under 35 U.S.C. 154(b) by 662 days.

(21) Appl. No.: 11/350,703

(22) Filed: Feb. 8, 2006

(65) Prior Publication Data

US 2006/0135428 A1 Jun. 22, 2006

Related U.S. Application Data

(63) Continuation of application No. 09/623,543, filed as application No. PCT/IB00/00763 on May 15, 2000, now abandoned, application No. 11/350,703, which is a continuation of application No. 09/657,431, filed on Sep. 7, 2000, now Pat. No. 7,144,854.

(60) Provisional application No. 60/159,783, filed on Oct. 15, 1999, provisional application No. 60/134,406, filed on May 17, 1999.

(51) Int. Cl.
A61K 38/00 (2006.01)
(52) U.S. Cl. ......................................................... 514/12
(58) Field of Classification Search .................... 514/12
See application file for complete search history.

(56) References Cited

U.S. PATENT DOCUMENTS

| 4,462,941 | A | | 7/1984 | Lee et al. |
| 5,116,944 | A | * | 5/1992 | Sivam et al. ................. 530/362 |
| 5,424,286 | A | | 6/1995 | Eng |
| 5,493,007 | A | | 2/1996 | Burnier et al. |
| 5,580,853 | A | | 12/1996 | Sytkowski |
| 5,612,034 | A | | 3/1997 | Pouletty et al. |
| 5,639,725 | A | | 6/1997 | O'Reilly et al. |
| 5,654,276 | A | | 8/1997 | Barrett et al. |
| 5,733,876 | A | | 3/1998 | O'Reilly et al. |
| 5,776,704 | A | | 7/1998 | O'Reilly et al. |
| 5,792,845 | A | | 8/1998 | O'Reilly et al. |
| 5,801,146 | A | | 9/1998 | Davidson |
| 5,837,682 | A | | 11/1998 | Folkman et al. |
| 5,840,733 | A | | 11/1998 | Krantz et al. |
| 5,843,440 | A | | 12/1998 | Pouletty et al. |
| 5,854,221 | A | | 12/1998 | Cao et al. |
| 5,864,372 | A | | 1/1999 | Chen et al. |
| 5,885,795 | A | | 3/1999 | O'Reilly et al. |
| 5,942,620 | A | | 8/1999 | Krantz et al. |
| 5,945,403 | A | | 8/1999 | Folkman et al. |
| 5,972,896 | A | | 10/1999 | Davidson |
| 5,981,484 | A | | 11/1999 | Davidson |
| 6,024,688 | A | | 2/2000 | Folkman et al. |
| 6,057,122 | A | | 5/2000 | Davidson |
| 6,087,375 | A | | 7/2000 | Bridon et al. |
| 6,103,233 | A | | 8/2000 | Pouletty et al. |
| 6,107,489 | A | | 8/2000 | Krantz et al. |
| 6,277,583 | B1 | | 8/2001 | Krantz et al. |
| 6,277,863 | B1 | | 8/2001 | Krantz et al. |
| 6,284,725 | B1 | | 9/2001 | Coolidge et al. |
| 6,329,336 | B1 | | 12/2001 | Bridon et al. |
| 6,403,324 | B1 | | 6/2002 | Krantz et al. |
| 6,437,092 | B1 | | 8/2002 | Ezrin et al. |
| 6,440,417 | B1 | | 8/2002 | Thibaudeau et al. |
| 6,451,974 | B1 | | 9/2002 | Hansen |
| 6,500,918 | B2 | | 12/2002 | Ezrin et al. |
| 6,514,500 | B1 | | 2/2003 | Bridon et al. |
| 6,593,295 | B2 | | 7/2003 | Bridon et al. |
| 6,602,981 | B2 | | 8/2003 | Ezrin et al. |
| 6,610,825 | B2 | | 8/2003 | Ezrin et al. |
| 6,706,892 | B1 | | 3/2004 | Ezrin et al. |
| 6,723,530 | B1 | | 4/2004 | Drucker |
| 6,767,887 | B1 | | 7/2004 | Hoffmann et al. |
| 6,821,949 | B2 | | 11/2004 | Bridon et al. |
| 6,849,714 | B1 | | 2/2005 | Bridon et al. |
| 6,887,470 | B1 | | 5/2005 | Bridon et al. |
| 6,887,849 | B2 | | 5/2005 | Bridon et al. |
| 7,090,851 | B1 | | 8/2006 | Bridon et al. |
| 7,112,567 | B2 | | 9/2006 | Bridon et al. |

(Continued)

FOREIGN PATENT DOCUMENTS

EP 0602290 6/1994

(Continued)

OTHER PUBLICATIONS

Peeters et al. (J. Immunol Methods 1989; 120: 133-143).*
Narazaki et al .(Pharmaceutical Research 1997; 14: 351-353).*
Bridon, et al., U.S. Appl. No. 09/623,543, filed Sep. 5, 2000.
Anti-Cancer Drugs, 1997, 8, 677-685.
Bailey, P.D., (1990) *An Introduction to Peptide Chemistry*, John Wiley & Sons, Inc., New York, NY, pp. 132-133.
Cancer Research, 1986, 46, 467-473.

(Continued)

*Primary Examiner*—Brandon J Fetterolf
(74) *Attorney, Agent, or Firm*—Jones Day

(57) ABSTRACT

Modified anti-angiogenic peptides are disclosed. The modified peptides are capable of forming a peptidase stabilized anti-angiogenic peptide. The modified anti-angiogenic peptides, particularly modified kringle 5 peptides are capable of forming a conjugate with a blood protein. Conjugates are prepared from anti-angiogenic peptides, particularly kringle 5 peptides, by combining the peptide with a reactive functional group with a blood protein. The conjugates may be formed in vivo or ex vivo. The conjugates are administered to patients to provide an anti-angiogenic effect.

18 Claims, No Drawings

U.S. PATENT DOCUMENTS

| | | | |
|---|---|---|---|
| 7,144,854 B1 * | 12/2006 | Bridon et al. | 514/2 |
| 7,166,695 B2 | 1/2007 | Krantz et al. | |
| 7,256,253 B2 * | 8/2007 | Bridon et al. | 530/300 |
| 7,268,113 B2 | 9/2007 | Bridon et al. | |
| 7,307,148 B2 | 12/2007 | Bousquet-Gagnon et al. | |
| 2003/0170250 A1 | 9/2003 | Ezrin et al. | |
| 2004/0127398 A1 | 7/2004 | Bridon et al. | |
| 2004/0138100 A1 | 7/2004 | Bridon et al. | |
| 2004/0156859 A1 | 8/2004 | Ezrin et al. | |
| 2004/0266673 A1 | 12/2004 | Bakis et al. | |
| 2005/0065075 A1 | 3/2005 | Erickson et al. | |
| 2005/0070475 A1 | 3/2005 | Bridon et al. | |
| 2005/0176641 A1 | 8/2005 | Bakis et al. | |
| 2005/0176643 A1 | 8/2005 | Bridon et al. | |
| 2006/0058235 A1 | 3/2006 | Bridon et al. | |
| 2006/0135426 A1 | 6/2006 | Bridon et al. | |
| 2006/0135428 A1 | 6/2006 | Bridon et al. | |
| 2006/0217304 A1 | 9/2006 | Bridon et al. | |
| 2006/0241019 A1 | 10/2006 | Bridon et al. | |
| 2007/0207958 A1 | 9/2007 | Bridon et al. | |
| 2007/0269863 A1 | 11/2007 | Bridon et al. | |

FOREIGN PATENT DOCUMENTS

| | | |
|---|---|---|
| WO | WO 91/08220 | 6/1991 |
| WO | WO-95/10302 | 4/1995 |
| WO | WO 97/25074 | 1/1997 |
| WO | WO 97/29372 | 1/1997 |
| WO | WO-97/23500 | 7/1997 |
| WO | WO-97/41284 | 11/1997 |
| WO | WO-97/41824 | 11/1997 |
| WO | WO 9741824 A2 * | 11/1997 |
| WO | WO 97/46584 | 12/1997 |
| WO | WO 98/00171 | 1/1998 |
| WO | WO 98/05351 | 2/1998 |
| WO | WO 98/11437 | 3/1998 |
| WO | WO 99/24076 | 11/1998 |
| WO | WO-98/54217 | 12/1998 |
| WO | WO-99/00420 | 1/1999 |
| WO | WO 99/07404 | 2/1999 |
| WO | WO 99/24071 | 5/1999 |
| WO | WO-99/24074 | 5/1999 |
| WO | WO-99/24075 | 5/1999 |
| WO | WO 99/24462 | 5/1999 |
| WO | WO 99/25727 | 5/1999 |
| WO | WO 99/25728 | 5/1999 |
| WO | WO 99/46283 | 5/1999 |
| WO | WO-99/48536 | 9/1999 |
| WO | WO-00/04052 | 1/2000 |
| WO | WO-00/13576 | 3/2000 |
| WO | WO 00/69902 | 5/2000 |
| WO | WO-00/47729 | 8/2000 |
| WO | WO-00/48595 | 8/2000 |
| WO | WO-00/54796 | 9/2000 |
| WO | WO-00/61179 | 10/2000 |
| WO | WO-00/69900 | 11/2000 |
| WO | WO 00/69911 | 11/2000 |
| WO | WO 01/17568 | 3/2001 |
| WO | WO 01/17614 | 3/2001 |
| WO | WO 02/62844 | 1/2002 |
| WO | WO 02/66511 | 2/2002 |
| WO | WO 02/96935 | 5/2002 |
| WO | WO 2004/011498 | 2/2004 |
| WO | WO 2005/012346 | 2/2005 |
| WO | WO 2005/103087 | 4/2005 |
| WO | WO 2005/108418 | 6/2005 |
| WO | WO 2007/053946 | 5/2007 |
| WO | WO 2007/071068 | 6/2007 |

OTHER PUBLICATIONS

Dermer, Gerard B., (Mar. 1994) "Another Anniversary for the War on Cancer," Bio/Technology, 12: 320.

Humphries, Martin J. et al., (1994) "Conjugation of synthetic peptides to carrier proteins for cell adhesion studies," J. Tissue Culture Methods, 16: 239-242.

J. Natl. Cancer Institute, 1989, 82, 4-6.

Peeters, J. M. et al., (1989) "Comparison of four bifunctional reagents for coupling peptides to proteins and the effect of the three moieties on the immunogenicity of the conjugates," J. Immunol. Methods, 120:133-143.

Pietersz, Geoffrey A., (1990) "The Linkage of Cytotoxic Drugs to Monoclonal Antibodies for the Treatment of Cancer," Bioconjugate Chemistry, 1(2):89-94.

Yeh, Patrice et al., (Mar. 1992) "Design of yeast-secreted albumin derivatives for human therapy: Biological and antiviral properties of serum albumin-CD4 genetic conjugate," Proc. Natl. Acad. Sci. USA, 89: 1904-1908.

U.S. Appl. No. 60/037,412, filed Feb. 5, 1997, Drucker.
U.S. Appl. No. 60/103,498, filed Oct. 8, 1998, Coolidge et al.
U.S. Appl. No. 60/132,018, filed Apr. 30, 1999, Prickett et al.
U.S. Appl. No. 60/152,681, filed Sep. 7, 1999, Ezrin et al.
U.S. Appl. No. 09/424,571, filed Nov. 22, 1999, Ezrin et al.

Alberts et al., 1994, *Molecular Biology of the Cell, Third Edition*. New York: Garland Publishing, p. G19.

Barragán et al., 1996, "Interactions of Exendin(9-39) with the Effects of Glucagon-Like Peptide-l-(7-36) Amide and of Exendin-4 on Arterial Blood Pressure and Heart Rate in Rats," 67:63-68.

Binder et al., 1984, "Insulin Pharmacokinetics," *Diabetes Care* 7:188-199.

Breton et al., 1995, "Prolonged Half-Life in the Circulation of a Chemical Conjugate Between a Pro-Urokinase Derivative and Human Serum Albumin," *Eur. J. Biochem.* 231:563-569.

*Catalog, Shearwater Polymers, Inc., Functionalized Biocompatible Polymers for Research, Polyethylene Glycol Derivatives*, 1993.

Cooper, 1997, *The Cell A Molecular Approach*, ASM Press (Washington, DC), Sinauer Associates, Inc. (Sunderland, MA), 296-298, 648.

Edwards et al., (Dec. 1998), "Glucagon-Like Peptide 1 Has a Physiological Role in the Control of Postprandial Glucose in Humans," *Diabetes* 48: 86-93.

Eng et al., 1990, "Purification and Structure of Exendin-3, a New Pancreatic Secretagogue Isolated from *Heloderma horridum*Venom," *J. Biol. Chem.* 265:20259-20262.

Eng et al., 1992, "Isolation and Characterization of Exendin-4, an Exendin-3 Analogue, from Heloderma suspectum Venom," *J. Biol. Chem.* 267:7402-7405.

Gennaro, ed., 1995, *Remington: The Science and Practice of Pharmacy, 19th Edition*, 898, 931-94.

Göke et al., 1989, "Characterization of the Receptor for Glucagon-like-peptide-1(7-36)amide on Plasma Membranes from Rat Insulinoma-derived Cells by Covalent Cross-Linking," *J. Mol. Endocrinol*. 2:93-98.

Göke et al., 1992, "Solubilization of Active GLP-1 (7-36)amide Receptors From RINm5F Plasma Membranes," *FEBS Lett*. 300:232-236.

Göke et al., 1993, "Exendin-4 is a High Potency Agonist and Truncated Exendin-(9-39)-amide an Antagonist at the Glucagon-like Peptide 1-(7-36)-amide Receptor of Insulin-secreting β-Cells," *J. Biol. Chem.* 268(26):19650-19655.

Göke et al., 1995, "Distribution of GLP-1 Binding Sites in the Rat Brain: Evidence that Exendin-4 is a Ligand of Brain GLP-1 Binding Sites," *Eur. J. Neurosci*. 7:2294-2300.

Gombotz and Pettit, 1995, "Biodegradable Polymers for Protein and Peptide Drug Delivery," *Bioconjugate Chem*. 6:332-351.

Grand, 1989, "Acylation of Viral and Eukaryotic Proteins," *Biochem J*. 258:625-638.

Grieg et al., (Jan. 1999), "Once Daily Injection of Exendin-4 to Diabetic Mice Achieves Long-Term Beneficial Effects of Blood Glucose Concentrations," *Diabetologia* 42:45-50.

Harlow & Lane, 1988, *Antibodies:A Laboratory Manual*, pp. 101, 129.

Hoshino et al., 1984, "Primary Structure of Helodermin, a VIP-Secretin-Like Peptide Isolated from Gila Monster Venom," *FEBS Lett.* 178:233-239.

Isoai et al., 1993, "A Potent Anti-Metastatic Activity of Tumor Invasion-Inhibiting Factor-2 and Albumin Conjugate," *Biochem. Biophys. Res. Comm.* 192:7-14.

Lewis, 1997, *Hawley's Condensed Chemical Dictionary, 13th Edition*, John Wiley & Sons, Inc. (New York), 487, 815.

Mattson et al., 1993, "A Practical Approach to Crosslinking," *Mol. Biol. Reports* 17:167-183.

Petrella et al., (May 1999), "Development and Validation of an Immunoradiometric Assay (IRMA) for the Quantitation of Exendin-4 in Plasma and Its Application to Preclinical Toxicity and Phase I Clinical Evaluations," Diabetes 48:A425.

Poznansky & Juliano, 1984, "Biological Approaches to the Controlled Delivery of Drugs: A Critical Review," *Pharmacological Reviews* 36:277-335.

Raufman, 1996, "Bioactive Peptides from Lizard Venoms," *Regulatory Peptides* 61:1-18.

Richter et al., 1991, "Characterization of Glucagon-Like Peptide-I(7-36)amide Receptors of Rat Lung Membranes by Covalent Cross-Linking," *FEBS Lett.* 280:247-250.

Robberecht et al., 1985, "Immunoreactive Helodermin-like Peptides in Rat: A New Class of Mammalian Neuropeptides Related to Secretin and VIP" *Biochem Biophys. Res. Comm.* 130: 333-342.

Schirra et al., 1998, "Exendin(9-39)amide is an Antagonist of Glucagon-Like Peptide-1(7-36)amide in Humans," *J. Clin. Invest.* 101:1421-1430.

Schmidtler et al., 1994, "Rat Parietal Cell Receptors for GLP-I-(7-36) Amide: Northern Blot, Cross-Linking, and Radioligand Binding," *Am. J. Physiol.* 267:G423-432.

Syed et al., 1997, "Potent Antithrombin Activity and Delayed Clearance From the Circulation Characterize Recombinant Hirudin Genetically Fused to Albumin," *Blood* 89:3243-3252.

Vandermeers et al., 1984, "Purification of a Novel Pancreatic Secretory Factor (PSF) and a Novel Peptide with VIP- and Secretin-like Properties (Helodermin) from Gila Monster Venom," *FEBS Lett.* 166:273-276.

Vandermeers et al., 1987, "Chemical, Immunological and Biological Properties of Peptides Like Vasoactive-Intestinal-Peptide and Peptide-Histidine-Isoleucinamide Extracted from the Venom of Two Lizards (*Heloderma horridum* and *Heloderma suspectum*)," *Eur. J Biochem.* 164:321-327.

Meloun et al., 1975, "Complete Amino Acid Sequence of Human Serum Albumin," *FEBS Letters* 58, 134-137.

Davis et al., 1991, "Reduction of Immunogenicity and extension of circulating half-life of peptides and proteins," Peptide and Protein Drug Delivery, Marcel Dekker, Inc., NY, NY, 831-864.

Paige et al., 1995, "Prolonged circulation of recombinant human granulocyte-colony stimulating factor by covalent linkage to albumin through a heterobifunctional polyethylene glycol," *Pharm. Research.*, vol. 12(12), 1883-1888.

Poznansky, 1983, "Enzyme-protein conjugates: new possibilities for enzyme therapy," *Pharm. Ther.*, vol. 21, pp. 53-76.

Poznansky et al., 1988, "Growth hormone-albumin conjugates reduced renal toxicity and altered plasma clearance," Federation of European Biochemical Societies, vol. 239(1), pp. 18-22.

Hermanson. G.T., "Chapter 9: Preparation of Hapten-Carrier Immunogen Conjugates" in Bioconjugate Techniques, 1996, pp. 421-426 (Academic Press, San Diego, CA).

* cited by examiner

SEQUENCE LISTING

<160> NUMBER OF SEQ ID NOS: 67

<210> SEQ ID NO 1
<211> LENGTH: 790
<212> TYPE: PRT
<213> ORGANISM: Artificial Sequence
<220> FEATURE:
<223> OTHER INFORMATION: Synthetic Peptide

<400> SEQUENCE: 1

Glu Pro Leu Asp Asp Tyr Val Asn Thr Gln Gly Ala Ser Leu Phe Ser

-continued

```
  1               5                  10                 15
Val Thr Lys Lys Gln Leu Gly Ala Gly Ser Ile Glu Glu Cys Ala Ala
                20                 25                 30

Lys Cys Glu Glu Asp Glu Glu Phe Thr Cys Arg Ala Phe Gln Tyr His
             35                 40                 45

Ser Lys Glu Gln Gln Cys Val Ile Met Ala Glu Asn Arg Lys Ser Ser
         50                 55                 60

Ile Ile Ile Arg Met Arg Asp Val Val Leu Phe Glu Lys Lys Val Tyr
 65                 70                 75                 80

Leu Ser Glu Cys Lys Thr Gly Asn Gly Lys Asn Tyr Arg Gly Thr Ser
                 85                 90                 95

Lys Thr Lys Asn Gly Ile Thr Cys Gln Lys Trp Ser Ser Thr Ser Pro
             100                105                110

His Arg Pro Arg Phe Ser Pro Ala Thr His Pro Ser Glu Gly Leu Glu
         115                120                125

Glu Asn Tyr Cys Arg Asn Pro Asp Asn Asp Pro Gln Gly Pro Trp Cys
     130                135                140

Tyr Thr Thr Asp Pro Glu Lys Arg Tyr Asp Tyr Cys Asp Ile Leu Glu
145                150                155                160

Cys Glu Glu Glu Cys Met His Cys Ser Gly Glu Asn Tyr Asp Gly Lys
                165                170                175

Ile Ser Lys Thr Met Ser Gly Leu Glu Cys Gln Ala Trp Asp Ser Gln
             180                185                190

Ser Pro His Ala His Gly Tyr Ile Pro Ser Lys Phe Pro Asn Lys Asn
         195                200                205

Leu Lys Lys Asn Tyr Cys Arg Asn Pro Asp Arg Glu Leu Arg Pro Trp
     210                215                220

Cys Phe Thr Thr Asp Pro Asn Lys Arg Trp Glu Leu Cys Asp Ile Pro
225                230                235                240

Arg Cys Thr Thr Pro Pro Ser Ser Gly Pro Thr Tyr Gln Cys Leu
                245                250                255

Lys Gly Thr Gly Glu Asn Tyr Arg Gly Asn Val Ala Val Thr Val Ser
             260                265                270

Gly His Thr Cys Gln His Trp Ser Ala Gln Thr Pro His Thr His Asn
         275                280                285

Arg Thr Pro Glu Asn Phe Pro Cys Lys Asn Leu Asp Glu Asn Tyr Cys
     290                295                300

Arg Asn Pro Asp Gly Lys Arg Ala Pro Trp Cys His Thr Thr Asn Ser
305                310                315                320

Gln Val Arg Trp Glu Tyr Cys Lys Ile Pro Ser Cys Asp Ser Ser Pro
                325                330                335

Val Ser Thr Glu Gln Leu Ala Pro Thr Ala Pro Pro Glu Leu Thr Pro
             340                345                350

Val Val Gln Asp Cys Tyr His Gly Asp Gly Gln Ser Tyr Arg Gly Thr
         355                360                365

Ser Ser Thr Thr Thr Thr Gly Lys Lys Cys Gln Ser Trp Ser Ser Met
     370                375                380

Thr Pro His Arg His Gln Lys Thr Pro Glu Asn Tyr Pro Asn Ala Gly
385                390                395                400

Leu Thr Met Asn Tyr Cys Arg Asn Pro Asp Ala Asp Lys Gly Pro Trp
                405                410                415

Cys Phe Thr Thr Asp Pro Ser Val Arg Trp Glu Tyr Cys Asn Leu Lys
             420                425                430
```

```
Lys Cys Ser Gly Thr Glu Ala Ser Val Val Ala Pro Pro Val Val
            435                 440                 445
Leu Leu Pro Asp Val Glu Thr Pro Ser Glu Glu Asp Cys Met Phe Gly
450                 455                 460
Asn Gly Lys Gly Tyr Arg Gly Lys Arg Ala Thr Thr Val Thr Gly Thr
465                 470                 475                 480
Pro Cys Gln Asp Trp Ala Ala Gln Glu Pro His Arg His Ser Ile Phe
                485                 490                 495
Thr Pro Glu Thr Asn Pro Arg Ala Gly Leu Glu Lys Asn Tyr Cys Arg
            500                 505                 510
Asn Pro Asp Gly Asp Val Gly Gly Pro Trp Cys Tyr Thr Thr Asn Pro
            515                 520                 525
Arg Lys Leu Tyr Asp Tyr Cys Asp Val Pro Gln Cys Ala Ala Pro Ser
        530                 535                 540
Phe Asp Cys Gly Lys Pro Gln Val Glu Pro Lys Lys Cys Pro Gly Arg
545                 550                 555                 560
Val Val Gly Gly Cys Val Ala His Pro His Ser Trp Pro Trp Gln Val
                565                 570                 575
Ser Leu Arg Thr Arg Phe Gly Met His Phe Cys Gly Gly Thr Leu Ile
            580                 585                 590
Ser Pro Glu Trp Val Leu Thr Ala Ala His Cys Leu Glu Lys Ser Pro
        595                 600                 605
Arg Pro Ser Ser Tyr Lys Val Ile Leu Gly Ala His Gln Glu Val Asn
    610                 615                 620
Leu Glu Pro His Val Gln Glu Ile Glu Val Ser Arg Leu Phe Leu Glu
625                 630                 635                 640
Pro Thr Arg Lys Asp Ile Ala Leu Leu Lys Leu Ser Ser Pro Ala Val
                645                 650                 655
Ile Thr Asp Lys Val Ile Pro Ala Cys Leu Pro Ser Pro Asn Tyr Val
            660                 665                 670
Val Ala Asp Arg Thr Glu Cys Phe Ile Thr Gly Trp Gly Glu Thr Gln
        675                 680                 685
Gly Thr Phe Gly Ala Gly Leu Leu Lys Glu Ala Gln Leu Pro Val Ile
    690                 695                 700
Glu Asn Lys Val Cys Asn Arg Tyr Glu Phe Leu Asn Gly Arg Val Gln
705                 710                 715                 720
Ser Thr Glu Leu Cys Ala Gly His Leu Ala Gly Gly Thr Asp Ser Cys
                725                 730                 735
Gln Gly Asp Ser Gly Gly Pro Leu Val Cys Phe Glu Lys Asp Lys Tyr
            740                 745                 750
Ile Leu Gln Gly Val Thr Ser Trp Gly Leu Gly Cys Ala Arg Pro Asn
        755                 760                 765
Lys Pro Gly Val Tyr Val Arg Val Ser Arg Phe Val Thr Trp Ile Glu
    770                 775                 780
Gly Val Met Arg Asn Asn
785                 790

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2
```

```
Pro Arg Lys Leu Tyr Asp Lys
 1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3

Tyr Thr Thr Asn Pro Arg Lys Leu Tyr Asp Tyr Lys
 1               5                  10

<210> SEQ ID NO 4
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 4

Arg Asn Pro Asp Gly Asp Val Gly Gly Pro Trp Ala Tyr Thr Thr Asn
 1               5                  10                  15

Pro Arg Lys Leu Tyr Asp Tyr Lys
            20

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Arg Asn Pro Asp Gly Asp Val Gly Gly Pro Trp Lys
 1               5                  10

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Pro Arg Lys Leu Tyr Asp Tyr Lys
 1               5

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 7

Tyr Thr Thr Asn Pro Arg Lys Leu Tyr Asp Tyr Lys
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide
```

```
-continued

<400> SEQUENCE: 8

Tyr Thr Thr Asn Pro Arg Lys Leu Tyr Asp Tyr
1               5                   10

<210> SEQ ID NO 9
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 9

Arg Asn Pro Asp Gly Asp Val Gly Gly Pro Trp Ala Tyr Thr Thr Asn
1               5                   10                  15

Pro Arg Lys Leu Tyr Asp Tyr
            20

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 10

Arg Lys Leu Tyr Asp Tyr Lys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 11

Arg Lys Leu Tyr Asp Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 12

Pro Arg Lys Leu Tyr Asp Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 13

Pro Arg Lys Leu Tyr Asp
1               5

<210> SEQ ID NO 14
<211> LENGTH: 8
<212> TYPE: PRT
<213> ORGANISM: Artificial Sequence
```

```
<220> FEATURE:
<223> OTHER INFORMATION: Synthetic Peptide

<400> SEQUENCE: 14

Pro Arg Lys Leu Tyr Asp Tyr Lys
 1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

Pro Arg Lys Leu Tyr Asp Tyr
 1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 16

Arg Asn Pro Asp Gly Asp Val Gly Gly Pro Trp
 1               5                   10

<210> SEQ ID NO 17
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is NAc-Pro

<400> SEQUENCE: 17

Pro Arg Lys Leu Tyr Asp Lys
 1               5

<210> SEQ ID NO 18
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg

<400> SEQUENCE: 18

Arg Lys Leu Tyr Asp Tyr Lys
 1               5

<210> SEQ ID NO 19
<211> LENGTH: 12
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Tyr is NAc-Tyr
```

```
<400> SEQUENCE: 19

Tyr Thr Thr Asn Pro Arg Lys Leu Tyr Asp Tyr Lys
1               5                   10

<210> SEQ ID NO 20
<211> LENGTH: 24
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg

<400> SEQUENCE: 20

Arg Asn Pro Asp Gly Asp Val Gly Gly Pro Trp Ala Tyr Thr Thr Asn
1               5                   10                  15

Pro Arg Lys Leu Tyr Asp Tyr Lys
            20

<210> SEQ ID NO 21
<211> LENGTH: 12
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg

<400> SEQUENCE: 21

Arg Asn Pro Asp Gly Asp Val Gly Gly Pro Trp Lys
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is NAc-Pro
<220> FEATURE:
<221> NAME/KEY: SITE
<222> LOCATION: 8
<223> OTHER INFORMATION: Lys is Lys-(N-MPA)-NH2; MPA is attached to the
      epsilon carbon amino group

<400> SEQUENCE: 22

Pro Arg Lys Leu Tyr Asp Tyr Lys
1               5

<210> SEQ ID NO 23
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is (MPA-AEEA)-Pro

<400> SEQUENCE: 23
```

```
Pro Arg Lys Leu Tyr Asp Tyr
 1               5
```

<210> SEQ ID NO 24
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is (MPA)-Pro

<400> SEQUENCE: 24

```
Pro Arg Lys Leu Tyr Asp Tyr
 1               5
```

<210> SEQ ID NO 25
<211> LENGTH: 12
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Tyr is NAc-Tyr
<220> FEATURE:
<221> NAME/KEY: SITE
<222> LOCATION: 12
<223> OTHER INFORMATION: Lys is Lys-(N-MPA)-NH2; MPA is attached to the
      epsilon carbon amino group

<400> SEQUENCE: 25

```
Tyr Thr Thr Asn Pro Arg Lys Leu Tyr Asp Tyr Lys
 1               5                  10
```

<210> SEQ ID NO 26
<211> LENGTH: 11
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Tyr is (MPA-AEEA)-Tyr

<400> SEQUENCE: 26

```
Tyr Thr Thr Asn Pro Arg Lys Leu Tyr Asp Tyr
 1               5                  10
```

<210> SEQ ID NO 27
<211> LENGTH: 11
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Tyr is (MPA)-Tyr

<400> SEQUENCE: 27

```
Tyr Thr Thr Asn Pro Arg Lys Leu Tyr Asp Tyr
 1               5                  10
```

<210> SEQ ID NO 28
<211> LENGTH: 24

```
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg
<220> FEATURE:
<221> NAME/KEY: SITE
<222> LOCATION: 24
<223> OTHER INFORMATION: Lys is Lys-(N-MPA)-NH2; MPA is attached to the
      epsilon carbon amino group

<400> SEQUENCE: 28

Arg Asn Pro Asp Gly Asp Val Gly Gly Pro Trp Ala Tyr Thr Thr Asn
1               5                   10                  15

Pro Arg Lys Leu Tyr Asp Tyr Lys
            20

<210> SEQ ID NO 29
<211> LENGTH: 23
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA-AEEA)-Arg

<400> SEQUENCE: 29

Arg Asn Pro Asp Gly Asp Val Gly Gly Pro Trp Ala Tyr Thr Thr Asn
1               5                   10                  15

Pro Arg Lys Leu Tyr Asp Tyr
            20

<210> SEQ ID NO 30
<211> LENGTH: 23
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA)-Arg

<400> SEQUENCE: 30

Arg Asn Pro Asp Gly Asp Val Gly Gly Pro Trp Ala Tyr Thr Thr Asn
1               5                   10                  15

Pro Arg Lys Leu Tyr Asp Tyr
            20

<210> SEQ ID NO 31
<211> LENGTH: 12
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg
<220> FEATURE:
<221> NAME/KEY: SITE
<222> LOCATION: 12
<223> OTHER INFORMATION: Lys is Lys-(N-MPA)-NH2; MPA is attached to the
      epsilon carbon amino group
```

```
<400> SEQUENCE: 31

Arg Asn Pro Asp Gly Asp Val Gly Gly Pro Trp Lys
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA-AEEA)-Arg

<400> SEQUENCE: 32

Arg Asn Pro Asp Gly Asp Val Gly Gly Pro Trp
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA)-Arg

<400> SEQUENCE: 33

Arg Asn Pro Asp Gly Asp Val Gly Gly Pro Trp
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg
<220> FEATURE:
<221> NAME/KEY: SITE
<222> LOCATION: 7
<223> OTHER INFORMATION: Lys is Lys-(N-MPA)-NH2; MPA is attached to the
      epsilon carbon amino group

<400> SEQUENCE: 34

Arg Lys Leu Tyr Asp Tyr Lys
1               5

<210> SEQ ID NO 35
<211> LENGTH: 6
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA-AEEA)-Arg

<400> SEQUENCE: 35

Arg Lys Leu Tyr Asp Tyr
1               5
```

<210> SEQ ID NO 36
<211> LENGTH: 6
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA)-Arg

<400> SEQUENCE: 36

Arg Lys Leu Tyr Asp Tyr
1               5

<210> SEQ ID NO 37
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is NAc-Pro
<220> FEATURE:
<221> NAME/KEY: SITE
<222> LOCATION: 7
<223> OTHER INFORMATION: Lys is Lys-(N-MPA)-NH2; MPA is attached to the
      epsilon carbon amino group

<400> SEQUENCE: 37

Pro Arg Lys Leu Tyr Asp Lys
1               5

<210> SEQ ID NO 38
<211> LENGTH: 6
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is (MPA-AEEA)-Pro

<400> SEQUENCE: 38

Pro Arg Lys Leu Tyr Asp
1               5

<210> SEQ ID NO 39
<211> LENGTH: 6
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is (MPA)-Pro

<400> SEQUENCE: 39

Pro Arg Lys Leu Tyr Asp
1               5

<210> SEQ ID NO 40
<211> LENGTH: 8
<212> TYPE: PRT
<213> ORGANISM: Artificial Sequence
<220> FEATURE:
<223> OTHER INFORMATION: Modified kringle 5 peptide

```
<220> FEATURE:
<221> NAME/KEY: SITE
<222> LOCATION: 1
<223> OTHER INFORMATION: Pro is NAc-Pro
<220> FEATURE:
<221> NAME/KEY: SITE
<222> LOCATION: 8
<223> OTHER INFORMATION: Lys is Lys-(N-AEEA-MPA)-NH2; AEEA-MPA is
      attached to the epsilon carbon amino group

<400> SEQUENCE: 40

Pro Arg Lys Leu Tyr Asp Tyr Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is NAc-Pro
<220> FEATURE:
<221> NAME/KEY: SITE
<222> LOCATION: 8
<223> OTHER INFORMATION: Lys is Lys-(N-AEEAn-MPA)-NH2; AEEAn-MPA is
      attached to the epsilon carbon amino group

<400> SEQUENCE: 41

Pro Arg Lys Leu Tyr Asp Tyr Lys
1               5

<210> SEQ ID NO 42
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is NAc-Pro
<220> FEATURE:
<221> NAME/KEY: SITE
<222> LOCATION: 7
<223> OTHER INFORMATION: Lys is Lys-NH2.3TFA

<400> SEQUENCE: 42

Pro Arg Lys Leu Tyr Asp Lys
1               5

<210> SEQ ID NO 43
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg
<220> FEATURE:
<221> NAME/KEY: SITE
<222> LOCATION: 7
<223> OTHER INFORMATION: Lys is Lys-NH2.3TFA

<400> SEQUENCE: 43

Arg Lys Leu Tyr Asp Tyr Lys
1               5
```

<210> SEQ ID NO 44
<211> LENGTH: 12
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Tyr is NAc-Tyr
<220> FEATURE:
<221> NAME/KEY: SITE
<222> LOCATION: 12
<223> OTHER INFORMATION: Lys is Lys-NH2.3TFA

<400> SEQUENCE: 44

Tyr Thr Thr Asn Pro Arg Lys Leu Tyr Asp Tyr Lys
1               5                   10

<210> SEQ ID NO 45
<211> LENGTH: 24
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg
<220> FEATURE:
<221> NAME/KEY: SITE
<222> LOCATION: 24
<223> OTHER INFORMATION: Lys is Lys-NH2.4TFA

<400> SEQUENCE: 45

Arg Asn Pro Asp Gly Asp Val Gly Gly Pro Trp Ala Tyr Thr Thr Asn
1               5                   10                  15

Pro Arg Lys Leu Tyr Asp Tyr Lys
            20

<210> SEQ ID NO 46
<211> LENGTH: 12
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg
<220> FEATURE:
<221> NAME/KEY: SITE
<222> LOCATION: 12
<223> OTHER INFORMATION: Lys is Lys-NH2.2TFA

<400> SEQUENCE: 46

Arg Asn Pro Asp Gly Asp Val Gly Gly Pro Trp Lys
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is NAc-Pro
<220> FEATURE:
<221> NAME/KEY: SITE

```
<222> LOCATION: 8
<223> OTHER INFORMATION: Lys is Lys-(N-MPA)-NH2.2TFA; MPA is attached to
      the epsilon carbon amino group

<400> SEQUENCE: 47

Pro Arg Lys Leu Tyr Asp Tyr Lys
1               5

<210> SEQ ID NO 48
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is (MPA-AEEA)-Pro
<220> FEATURE:
<221> NAME/KEY: SITE
<222> LOCATION: 7
<223> OTHER INFORMATION: Tyr is Tyr-NH2.2TFA

<400> SEQUENCE: 48

Pro Arg Lys Leu Tyr Asp Tyr
1               5

<210> SEQ ID NO 49
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is (MPA)-Pro
<220> FEATURE:
<221> NAME/KEY: SITE
<222> LOCATION: 7
<223> OTHER INFORMATION: Tyr is Tyr-NH2.2TFA

<400> SEQUENCE: 49

Pro Arg Lys Leu Tyr Asp Tyr
1               5

<210> SEQ ID NO 50
<211> LENGTH: 12
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Tyr is NAc-Tyr
<220> FEATURE:
<221> NAME/KEY: SITE
<222> LOCATION: 12
<223> OTHER INFORMATION: Lys is Lys-(N-MPA)-NH2.2TFA; MPA is attached to
      the epsilon carbon amino group

<400> SEQUENCE: 50

Tyr Thr Thr Asn Pro Arg Lys Leu Tyr Asp Tyr Lys
1               5                   10

<210> SEQ ID NO 51
<211> LENGTH: 11
<212> TYPE: PRT
<213> ORGANISM: Artificial Sequence
<220> FEATURE:
```

```
<223> OTHER INFORMATION: Modified kringle 5 peptide
<220> FEATURE:
<221> NAME/KEY: SITE
<222> LOCATION: 1
<223> OTHER INFORMATION: Tyr is (MPA-AEEA)-Tyr
<220> FEATURE:
<221> NAME/KEY: SITE
<222> LOCATION: 11
<223> OTHER INFORMATION: Tyr is Tyr-NH2.2TFA

<400> SEQUENCE: 51

Tyr Thr Thr Asn Pro Arg Lys Leu Tyr Asp Tyr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Tyr is (MPA)-Tyr
<220> FEATURE:
<221> NAME/KEY: SITE
<222> LOCATION: 11
<223> OTHER INFORMATION: Tyr is Tyr-NH2.2TFA

<400> SEQUENCE: 52

Tyr Thr Thr Asn Pro Arg Lys Leu Tyr Asp Tyr
1               5                   10

<210> SEQ ID NO 53
<211> LENGTH: 24
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg
<220> FEATURE:
<221> NAME/KEY: SITE
<222> LOCATION: 24
<223> OTHER INFORMATION: Lys is Lys-(N-MPA)-NH2.3TFA; MPA is attached to
      the epsilon carbon amino group

<400> SEQUENCE: 53

Arg Asn Pro Asp Gly Asp Val Gly Gly Pro Trp Ala Tyr Thr Thr Asn
1               5                   10                  15

Pro Arg Lys Leu Tyr Asp Tyr Lys
            20

<210> SEQ ID NO 54
<211> LENGTH: 23
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA-AEEA)-Arg
<220> FEATURE:
<221> NAME/KEY: SITE
<222> LOCATION: 23
<223> OTHER INFORMATION: Tyr is Tyr-NH2.3TFA

<400> SEQUENCE: 54
```

```
Arg Asn Pro Asp Gly Asp Val Gly Gly Pro Trp Ala Tyr Thr Thr Asn
1               5                   10                  15

Pro Arg Lys Leu Tyr Asp Tyr
            20

<210> SEQ ID NO 55
<211> LENGTH: 23
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: (MPA)-Arg
<220> FEATURE:
<221> NAME/KEY: SITE
<222> LOCATION: 23
<223> OTHER INFORMATION: Tyr is Tyr-NH2.3TFA

<400> SEQUENCE: 55

Arg Asn Pro Asp Gly Asp Val Gly Gly Pro Trp Ala Tyr Thr Thr Asn
1               5                   10                  15

Pro Arg Lys Leu Tyr Asp Tyr
            20

<210> SEQ ID NO 56
<211> LENGTH: 12
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg
<220> FEATURE:
<221> NAME/KEY: SITE
<222> LOCATION: 12
<223> OTHER INFORMATION: Lys is Lys-(N-MPA)-NH2.TFA; MPA is attached to
      the epsilon carbon amino group

<400> SEQUENCE: 56

Arg Asn Pro Asp Gly Asp Val Gly Gly Pro Trp Lys
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA-AEEA)-Arg
<220> FEATURE:
<221> NAME/KEY: SITE
<222> LOCATION: 11
<223> OTHER INFORMATION: Trp is Trp-NH2.TFA

<400> SEQUENCE: 57

Arg Asn Pro Asp Gly Asp Val Gly Gly Pro Trp
1               5                   10

<210> SEQ ID NO 58
<211> LENGTH: 11
<212> TYPE: PRT
<213> ORGANISM: Artificial Sequence
<220> FEATURE:
```

```
<223> OTHER INFORMATION: Modified kringle 5 peptide
<220> FEATURE:
<221> NAME/KEY: SITE
<222> LOCATION: 1
<223> OTHER INFORMATION: Arg is (MPA)-Arg
<220> FEATURE:
<221> NAME/KEY: SITE
<222> LOCATION: 11
<223> OTHER INFORMATION: Trp is Trp-NH2.TFA

<400> SEQUENCE: 58

Arg Asn Pro Asp Gly Asp Val Gly Gly Pro Trp
 1               5                   10

<210> SEQ ID NO 59
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is NAc-Arg
<220> FEATURE:
<221> NAME/KEY: SITE
<222> LOCATION: 7
<223> OTHER INFORMATION: Lys is Lys-(N-MPA)-NH2.2TFA; MPA is attached to
      the epsilon carbon amino group

<400> SEQUENCE: 59

Arg Lys Leu Tyr Asp Tyr Lys
 1               5

<210> SEQ ID NO 60
<211> LENGTH: 6
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA-AEEA)-Arg
<220> FEATURE:
<221> NAME/KEY: SITE
<222> LOCATION: 6
<223> OTHER INFORMATION: Tyr is Tyr-NH2.2TFA

<400> SEQUENCE: 60

Arg Lys Leu Tyr Asp Tyr
 1               5

<210> SEQ ID NO 61
<211> LENGTH: 6
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Arg is (MPA)-Arg
<220> FEATURE:
<221> NAME/KEY: SITE
<222> LOCATION: 6
<223> OTHER INFORMATION: Tyr is Tyr-NH2.2TFA

<400> SEQUENCE: 61

Arg Lys Leu Tyr Asp Tyr
 1               5
```

```
<210> SEQ ID NO 62
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is NAc-Pro
<220> FEATURE:
<221> NAME/KEY: SITE
<222> LOCATION: 7
<223> OTHER INFORMATION: Lys is Lys-(N-MPA)-NH2.2TFA; MPA is attached to
      the epsilon carbon amino group

<400> SEQUENCE: 62

Pro Arg Lys Leu Tyr Asp Lys
 1               5

<210> SEQ ID NO 63
<211> LENGTH: 6
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is (MPA-AEEA)-Pro
<220> FEATURE:
<221> NAME/KEY: SITE
<222> LOCATION: 6
<223> OTHER INFORMATION: Asp is Asp-NH2.2TFA

<400> SEQUENCE: 63

Pro Arg Lys Leu Tyr Asp
 1               5

<210> SEQ ID NO 64
<211> LENGTH: 6
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is (MPA)-Pro
<220> FEATURE:
<221> NAME/KEY: SITE
<222> LOCATION: 6
<223> OTHER INFORMATION: Asp is Asp-NH2.2TFA

<400> SEQUENCE: 64

Pro Arg Lys Leu Tyr Asp
 1               5

<210> SEQ ID NO 65
<211> LENGTH: 8
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is NAc-Pro
<220> FEATURE:
<221> NAME/KEY: SITE
<222> LOCATION: 8
<223> OTHER INFORMATION: Lys is Lys-(N-AEEA-MPA)-NH2.2TFA; AEEA-MPA is
```

-continued

```
      attached to the epsilon carbon amino group

<400> SEQUENCE: 65

Pro Arg Lys Leu Tyr Asp Tyr Lys
1               5

<210> SEQ ID NO 66
<211> LENGTH: 8
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is NAc-Pro
<220> FEATURE:
<221> NAME/KEY: SITE
<222> LOCATION: 8
<223> OTHER INFORMATION: Lys is Lys-(N-AEEAn-MPA)-NH2.2TFA; AEEAn-MPA is
      attached to the epsilon carbon amino group

<400> SEQUENCE: 66

Pro Arg Lys Leu Tyr Asp Tyr Lys
1               5

<210> SEQ ID NO 67
<211> LENGTH: 7
<212> TYPE: PRT
<213> ORGANISM: Artificial Sequence
<220> FEATURE:
<223> OTHER INFORMATION: Modified kringle 5 peptide
<220> FEATURE:
<221> NAME/KEY: SITE
<222> LOCATION: 1
<223> OTHER INFORMATION: Pro is (MPA)-Pro
<220> FEATURE:
<221> NAME/KEY: SITE
<222> LOCATION: 7
<223> OTHER INFORMATION: Lys is Lys-NH2.2TFA

<400> SEQUENCE: 67

Pro Arg Lys Leu Tyr Asp Lys
1               5
```

LONG LASTING ANTI-ANGIOGENIC PEPTIDES

RELATED APPLICATIONS

This application is a continuation of U.S. application Ser. No. 09/623,543, filed on Sep. 5, 2000, which is a National Stage of PCT/IB00/00763 filed on May 15, 2000, which claims the benefit under 35 U.S.C. 119(e) of U.S. Provisional Application No. 60/134,406, filed on May 17, 1999. This application is also a continuation of U.S. application Ser. No. 09/657,431, filed on Sep. 7, 2000, which claims the benefit under 35 U.S.C. 119(e) of U.S. Provisional Application Ser. No. 60/159,783, filed on Oct. 15, 1999. The contents of all the above cited patents and patent applications are hereby incorporated by reference in their entirety.

FIELD OF THE INVENTION

This invention relates to modified anti-angiogenic peptides. In particular, this invention relates to modified kringle 5 peptides with long duration of action for the treatment of diseases related to angiogenesis.

BACKGROUND OF THE INVENTION

Angiogenesis, the development of new blood vessels, is a highly regulated and essential process of endothelial cell growth. Although angiogenesis is a highly regulated process under normal conditions, many diseases (characterized as "angiogenic diseases") are driven by persistent unregulated angiogenesis. Unregulated, angiogenesis may either cause a particular disease directly or exascerbate an existing pathological condition. For example, ocular neovacularization has been implicated as the most common cause of blindness and dominates approximately 20 eye diseases. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J., Cancer Research, 46: 467473 (1986), Folkman, J., Journal of the National Cancer Institute, 82: 4-6 (1989)).

Much research has been performed to identify anti-antiogenic molecules. One angiogenic molecule of particular interest is plasminogen. Of particular interest is the kringle 5 region of plasminogen and various peptides within the kringle 5 region. Both plasminogen and the kringle 5 region of plasminogen have been shown to interfere with the angiogenic process are thus known as anti-angiogenic peptides.

While useful, kringle 5 peptides, like other peptides, suffer from rapid kidney excretion, liver metabolism, and decomposition from endogeneous peptidases leading to very short plasma half-lives thereby reducing their usefulness as anti-angiogenic agents. As a result of their short half lives, peptides such as kringle 5 require constant infusion to reach adequate plasma levels sufficient for efficient therapy.

As a result, there is a need for long lasting anti-angiogenic peptides such as kringle 5. Such long lasting peptides would be useful in treating angiogenesis related diseases in mammals.

SUMMARY OF THE INVENTION

In order to meet these needs, the present invention is directed to modified anti-angiogenic peptides. In particular, this invention is directed to modified kringle 5 peptides. The invention relates to novel chemically reactive derivatives of anti-angiogenic peptides that can react with available functionalities on mobile blood proteins to form covalent linkages. Specifically, the invention relates to novel chemically reactive derivatives of anti-angiogenic peptides such as kringle 5 peptides that can react with available functionalities on mobile blood proteins to form covalent linkages. The chemically reactive derivatives of the anti-angiogenic peptides are capable of forming a peptidase stabilized anti-angiogenic peptide.

The invention is directed to a derivative of an anti-angiogenic peptide such as a kringle 5 peptide where the derivative comprises a reactive group which reacts with amino groups, hydroxyl groups or thiol groups on blood proteins to form stable covalent bonds. In a preferred format, the anti-angiogenic peptides include succimidyl or maleimido reactive groups.

The present invention relates to modified kringle 5 peptides and derivatives thereof and their use as anti-angiogenic agents. The kringle 5 peptides include reactive groups capable of forming a covalent bond with mobile blood proteins.

In particular, the present invention relates to the following modified kringle 5 peptides: NAc-Pro-Arg-Lys-Leu-Tyr-Asp-Lys-NH$_2$; NAc-Arg-Lys-Leu-Tyr-Asp-Tyr-Lys-NH$_2$; Nac-Tyr-Thr-Thr-Asn-Pro-Arg-Lys-Leu-Tyr-Asp-Tyr-Lys-NH$_2$; NAc-Arg-Asn-Pro-Asp-Gly-Asp-Val-Gly-Gly-Pro-Trp-Ala-Tyr-Thr-Thr-Asn-Pro-Arg-Lys-Leu-Tyr-Asp-Tyr-Lys-NH$_2$; NAc-Arg-Asn-Pro-Asp-Gly-Asp-Val-Gly-Gly-Pro-Trp-Lys-NH$_2$; NAc-Pro-Arg-Lys-Leu-Tyr-Asp-Tyr-Lys-(Nϵ-MPA)-NH$_2$; (MPA-AEEA)-Pro-Arg-Lys-Leu-Tyr-Asp-Tyr-NH$_2$; (MPA)-Pro-Arg-Lys-Leu-Tyr-Asp-Tyr-NH$_2$; NAc-Tyr-Thr-Thr-Asn-Pro-Arg-Lys-Leu-Tyr-Asp-Tyr-Lys-(Nϵ-MPA)-NH$_2$; (MPA-AEEA)-Tyr-Thr-Thr-Asn-Pro-Arg-Lys-Leu-Tyr-Asp-Tyr-NH$_2$; MPA)-Tyr-Thr-Thr-Asn-Pro-Arg-Lys-Leu-Tyr-Asp-Tyr-NH$_2$; NAc-Arg-Asn-Pro-Asp-Gly-Asp-Val-Gly-Gly-Pro-Trp-Ala-Tyr-Thr-Thr-Asn-Pro-Arg-Lys-Leu-Tyr-Asp-Tyr-Lys-(Nϵ-MPA)-NH$_2$; (MPA-AEEA)-Arg-Asn-Pro-Asp-Gly-Asp-Val-Gly-Gly-Pro-Trp-Ala-Tyr-Thr-Thr-Asn-Pro-Arg-Lys-Leu-Tyr-Asp-Tyr-NH$_2$; (MPA)-Arg-Asn-Pro-Asp-Gly-Asp-Val-Gly-Gly-Pro-Trp-Ala-Tyr-Thr-Thr-Asn-Pro-Arg-Lys-Leu-Tyr-Asp-Tyr-NH$_2$; NAc-Arg-Asn-Pro-Asp-Gly-Asp-Val-Gly-Gly-Pro-Trp-Lys-(Nϵ-MPA)-NH$_2$; MPA-AEEA)-Arg-Asn-Pro-Asp-Gly-Asp-Val-Gly-Gly-Pro-Trp-NH$_2$; (MPA)-Arg-Asn-Pro-Asp-Gly-Asp-Val-Gly-Gly-Pro-Trp-NH$_2$; NAc-Arg-Lys-Leu-Tyr-Asp-Tyr-Lys-(Nϵ-MPA)-NH$_2$; (MPA-AEEA)-Arg-Lys-Leu-Tyr-Asp-Tyr-NH$_2$; (MPA)-Arg-Lys-Leu-Tyr-Asp-Tyr-NH$_2$; NAc-Pro-Arg-Lys-Leu-Tyr-Asp-Lys-(Nϵ-MPA)-NH$_2$; (MPA-AEEA)-Pro-Arg-Lys-Leu-Tyr-Asp-NH$_2$; (MPA)-Pro-Arg-Lys-Leu-Tyr-Asp-NH$_2$; NAc-Pro-Arg-Lys-Leu-Tyr-Asp-Tyr-Lys-(Nϵ-AEEA-MPA)-NH$_2$; NAc-Pro-Arg-Lys-Leu-Tyr-Asp-Tyr-Lys-(Nϵ-AEEA$_n$-MPA)-NH$_2$; and other modified kringle 5 peptides.

The modified anti-angiogenic peptides find use in the treatment of angiogenesis in humans.

DETAILED DESCRIPTION OF THE INVENTION

To ensure a complete understanding of the invention the following definitions are provided:

Reactive Groups: Reactive groups are chemical groups capable of forming a covalent bond. Such reactive groups are coupled or bonded to an anti-angiogenic, or, more specifically, a kringle 5 peptide of interest. Reactive groups will generally be stable in an aqueous environment and will usually be carboxy, phosphoryl, or convenient acyl group, either as an ester or a mixed anhydride, or an imidate, thereby capable of forming a covalent bond with functionalities such as an amino group, a hydroxy or a thiol at the target site on mobile blood components. For the most part, the esters will involve phenolic compounds, or be thiol esters, alkyl esters, phosphate esters, or the like.

Reactive groups include succimidyl and maleimido groups.

Functionalities: Functionalities are groups on blood components with which reactive groups react to form covalent bonds. Functionalities include hydroxyl groups for bonding to ester reactive groups; thiol groups for bonding to imidates and thioester groups; amino groups for bonding to carboxy, phosphoryl or acyl groups on reactive groups and carboxyl groups for bonding to amino groups.

Blood Components: Blood components may be either fixed or mobile. Fixed blood components are non-mobile blood components and include tissues, membrane receptors, interstitial proteins, fibrin proteins, collagens, platelets, endothelial cells, epithelial cells and their associated membrane and membraneous receptors, somatic body cells, skeletal and smooth muscle cells, neuronal components, osteocytes and osteoclasts and all body tissues especially those associated with the circulatory and lymphatic systems. Mobile blood components are blood components that do not have a fixed situs for any extended period of time, generally not exceeding 5, more specifically one minute. These blood components are not membrane-associated and are present in the blood for extended periods of time and are present in a minimum concentration of at least 0.1 µg/ml. Mobile blood components include serum albumin, transferrin, ferritin and immunoglobulins such as IgM and IgG. The half-life of mobile blood components is at least about 12 hours.

Protective Groups: Protective groups are chemical moieties utilized to protect peptide derivatives from reacting with themselves. Various protective groups are disclosed herein and in U.S. Pat. No. 5,493,007 which is hereby incorporated by reference. Such protective groups include acetyl, fluorenylmethyloxycarbonyl (FMOC), t-butyloxycarbonyl (BOC), benzyloxycarbonyl (CBZ), and the like. The specific protected amino acids are depicted in Table 1.

TABLE 1

NATURAL AMINO ACIDS AND THEIR ABBREVIATIONS

| Name | 3-Letter Abbreviation | 1-Letter Abbreviation | Protected Amino Acids |
|---|---|---|---|
| Alanine | Ala | A | Fmoc-Ala-OH |
| Arginine | Arg | R | Fmoc-Arg(Pbf)-OH |
| Asparagine | Asn | N | Fmoc-Asn(Trt)-OH |
| Aspartic acid | Asp | D | Asp(tBu)-OH |
| Cysteine | Cys | C | Fmoc-Cys(Trt) |
| Glutamic acid | Glu | E | Fmoc-Glu(tBu)-OH |
| Glutamine | Gln | Q | Fmoc-Gln(Trt)-OH |
| Glycine | Gly | G | Fmoc-Gly-OH |
| Histidine | His | H | Fmoc-His(Trt)-OH |
| Isoleucine | Ile | I | Fmoc-Ile-OH |
| Leucine | Leu | L | Fmoc-Leu-OH |
| Lysine | Lys | K | Fmoc-Lys(Mtt)-OH |
| Methionine | Met | M | Fmoc-Met-OH |
| Phenylalanine | Phe | F | Fmoc-Phe-OH |
| Proline | Pro | P | Fmoc-Pro-OH |
| Serine | Ser | S | Fmoc-Ser(tBu)-OH |
| Threonine | Thr | T | Fmoc-Thr(tBu)-OH |
| Tryptophan | Trp | W | Fmoc-Trp(Boc)-OH |
| Tyrosine | Tyr | Y | Boc-Tyr(tBu)-OH |
| Valine | Val | V | Fmoc-Val-OH |

Sensitive Functional Groups—A sensitive functional group is a group of atoms that represents a potential reaction site on an anti-angiogenic peptide. If present, a sensitive functional group may be chosen as the attachment point for the linker-reactive entity modification. Sensitive functional groups include but are not limited to carboxyl, amino, thiol, and hydroxyl groups.

Modified Peptides—A modified anti-angiogenic peptide is a peptide that has been modified by attaching a reactive group, and is capable of forming a peptidase stabilized peptide through conjugation to blood components. The reactive group may be attached to the anti-angiogenic peptide either via a linking group, or optionally without using a linking group. It is also contemplated that one or more additional amino acids may be added to the anti-angiogenic peptide to facilitate the attachment of the reactive group. Modified peptides may be administered in vivo such that conjugation with blood components occurs in vivo, or they may be first conjugated to blood components in vitro and the resulting peptidase stabilized peptide (as defined below) administered in vivo. The terms "modified anti-angiogenic peptide" and "modified peptide" may be used interchangeably in this application.

Peptidase Stabilized Anti-Angiogenic Peptides—A peptidase stabilized anti-angiogenic peptide is a modified peptide that has been conjugated to a blood component via a covalent bond formed between the reactive group of the modified peptide and the functionalities of the blood component, with or without a linking group. Peptidase stabilized peptides are more stable in the presence of peptidases in vivo than a non-stabilized peptide. A peptidase stabilized anti-angiogenic peptide generally has an increased half life of at least 10-50% as compared to a non-stabilized peptide of identical sequence. Peptidase stability is determined by comparing the half life of the unmodified anti-angiogenic peptide in serum or blood to the half life of a modified counterpart anti-angiogenic peptide in serum or blood. Half life is determined by sampling the serum or blood after administration of the modified and non-modified peptides and determining the activity of the peptide. In addition to determining the activity, the length of the anti-angiogenic peptide may also be measured by HPLC and Mass Spectrometry.

Linking Groups: Linking groups are chemical moieties that link or connect reactive groups to anti-angiogenic peptides. Linking groups may comprise one or more alkyl groups such as methyl, ethyl, propyl, butyl, etc. groups, alkoxy groups, alkenyl groups, alkynyl groups or amino group substituted by alkyl groups, cycloalkyl groups, polycyclic groups, aryl groups, polyaryl groups, substituted aryl groups, heterocyclic groups, and substituted heterocyclic groups. Linking groups may also comprise poly ethoxy aminoacids such as AEA ((2-amino) ethoxy acetic acid) or a preferred linking group AEEA ([2-(2-amino)ethoxy)]ethoxy acetic acid).

DETAILED DESCRIPTION OF THE INVENTION

Taking into account these definitions, the focus of this invention is to modify anti-angiogenic peptides and particularly kringle 5 peptides to improve bio-availability, extend half-life and distribution of the peptide in vivo through conjugation of the peptide onto a protein carrier without modifying its anti-angiogenesis properties. The carrier of choice (but not limited to) for this invention would be albumin conjugated through its free thiol by a kringle 5 peptide derivatized with a maleimide moiety.

1. Kringle 5 Peptides

As used herein, the term "kringle 5" refers to the region of mammalian plasminogen having three disulfide bonds which contribute to the specific three-dimensional confirmation defined by the fifth kringle region of the mammalian plasminogen molecule. One such disulfide bond links the cysteine residues located at amino acid positions 462 and 541, a second links the cysteine residues located at amino acid positions 483 and 524 and a third links the cysteine residues located at amino acid positions 512 and 536. The amino acid sequence of a complete mammalian plasminogen molecule (the human plasminogen molecule), including its kringle 5 region, is presented in (SEQ ID NO: 1).

The term "kringle 5 peptide fragments" refers to peptides with anti-angiogenic activity of between 4 and 104 amino acids (inclusive) with a substantial sequence homology to the corresponding peptide fragment of mammalian plasminogen, an α-N-terminus at about amino acid position 443 of intact mammalian plasminogen and an α-C-terminus at about position 546 of SEQ ID NO:1; an α-N-terminus at about amino acid position 513 of intact mammalian plasminogen and an α-C-terminus at about position 523 of SEQ ID NO:1; an α-N-terminus at about amino acid position 525 of intact mammalian plasminogen and an α-C-terminus at about position 535 of SEQ ID NO:1; an α-N-terminus at about amino acid position 529 of intact mammalian plasminogen and an α-C-terminus at about position 535 of SEQ ID NO:1; an α-N-terminus at about amino acid position 529 of intact mammalian plasminogen and an α-C-terminus at about position 534 of SEQ ID NO:1 and an α-N-terminus at about amino acid position 150 of intact mammalian plasminogen and an α-C-terminus at about position 156 of SEQ ID NO:1.

In a preferred format, the kringle 5 peptide of the invention has one or more of the following sequences:

```
Pro-Arg-Lys-Leu-Tyr-Asp-Lys-NH2;         (SEQ ID NO:2)

Tyr-Thr-Thr-Asn-Pro-Arg-Lys-Leu-Tyr-     (SEQ ID NO:3)
Asp-Tyr-Lys-NH2;

Arg-Asn-Pro-Asp-Gly-Asp-Val-Gly-Gly-     (SEQ ID NO:4)
Pro-Trp-Ala-Tyr-Thr-Thr-Asn-Pro-Arg-
Lys-Leu-Tyr-Asp-Tyr-Lys-NH2;

Arg-Asn-Pro-Asp-Gly-Asp-Val-Gly-Gly-     (SEQ ID NO:5)
Pro-Trp-Lys-NH2;

Pro-Arg-Lys-Leu-Tyr-Asp-Tyr-Lys-NH2;     (SEQ ID NO:6)

Tyr-Thr-Thr-Asn-Pro-Arg-Lys-Leu-Tyr-     (SEQ ID NO:7)
Asp-Tyr-Lys-NH2;

Tyr-Thr-Thr-Asn-Pro-Arg-Lys-Leu-Tyr-     (SEQ ID NO:8)
Asp-Tyr-NH2;

Arg-Asn-Pro-Asp-Gly-Asp-Val-Gly-Gly-     (SEQ ID NO:9)
Pro-Trp-Ala-Tyr-Thr-Thr-Asn-Pro-Arg-
Lys-Leu-Tyr-Asp-Tyr-NH2;

Arg-Lys-Leu-Tyr-Asp-Tyr-Lys-NH2;         (SEQ ID NO:10)

Arg-Lys-Leu-Tyr-Asp-Tyr-NH2;             (SEQ ID NO:11)

Pro-Arg-Lys-Leu-Tyr-Asp-Lys-NH2;         (SEQ ID NO:12)

Pro-Arg-Lys-Leu-Tyr-Asp-NH2;             (SEQ ID NO:13)

Pro-Arg-Lys-Leu-Tyr-Asp-Lys-NH2;         (SEQ ID NO:14)

Pro-Arg-Lys-Leu-Tyr-Asp-Tyr-NH2;         (SEQ ID NO:15)

and

Arg-Asn-Pro-Asp-Gly-Asp-Val-Gly-Gly-     (SEQ ID NO:16)
Pro-Trp.
```

Thus, it is to be understood that the present invention is contemplated to encompass any derivatives or modifications of kringle 5 peptide fragments which have anti-angiogenic activity and includes the entire class of kringle 5 peptide fragments described herein and derivatives and modifications of those kringle 5 peptide fragments.

2. Modified Kringle 5 Peptides

This invention relates to modified anti-angiogenic peptides and, in particular, modified kringle 5 peptides. The modified kringle 5 peptides of the invention can react with available reactive functionalities on blood components via covalent linkages. The invention also relates to such modifications, such combinations with blood components and methods for their use. These methods include extending the effective therapeutic in vivo half life of the modified kringle 5 peptides.

To form covalent bonds with the functional group on a protein, one may use as a chemically reactive group (reactive entity) a wide variety of active carboxyl groups, particularly esters, where the hydroxyl moiety is physiologically acceptable at the levels required to modify the kringle 5 peptide. While a number of different hydroxyl groups may be employed in these linking agents, the most convenient would be N-hydroxysuccinimide (NHS), N-hydroxy-sulfosuccinimide (sulfo-NHS), maleimide-benzoyl-succinimide (MBS), gamma-maleimido-butyryloxy succinimide ester (GMBS) and maleimidopropionic acid (MPA).

Primary amines are the principal targets for NHS esters as diagramed in the schematic below. Accessible α-amine groups present on the N-termini of proteins react with NHS esters. However, α-amino groups on a protein may not be desirable or available for the NHS coupling. While five amino acids have nitrogen in their side chains, only the ε-amine of lysine reacts significantly with NHS esters. An amide bond is formed when the NHS ester conjugation reaction reacts with primary amines releasing N-hydroxysuccinimide as demonstrated in the schematic below. These succinimide containing reactive groups are herein referred to as succinimidyl groups.

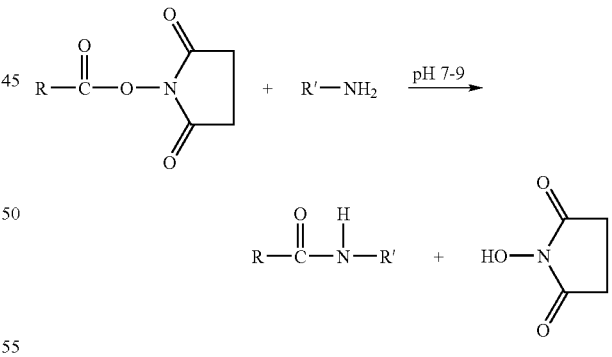

NHS-Ester Reaction Scheme

In the preferred embodiments of this invention, the functional group on the protein will be a thiol group and the chemically reactive group will be a maleimido-containing group such as gamma-maleimide butyrlamide (GMBA) or MPA. Such maleimide containing reactive groups are herein referred to as "maleimido groups." The maleimido group is most selective for sulfhydryl groups on peptides when the pH of the reaction mixture is kept between 6.5 and 7.4. At pH 7.0, the rate of reaction of maleimido groups with sulfhydryls is 1000-fold faster than with amines. A stable thioether linkage between the maleimido group and the sulfhydryl is formed which cannot be cleaved under physiological conditions as demonstrated in the following schematic.

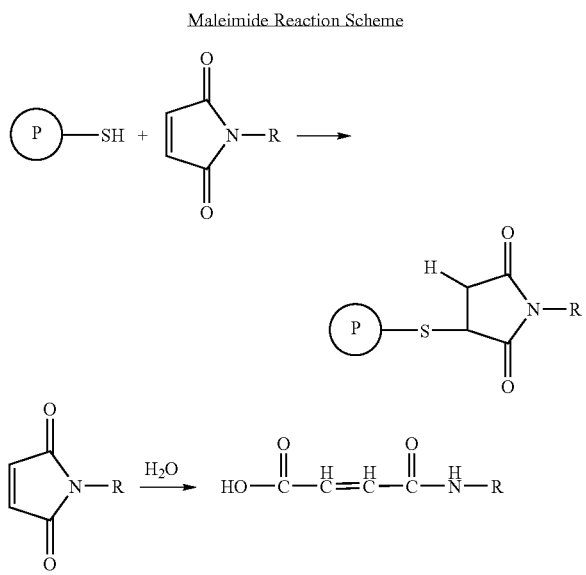

The kringle 5 peptides and peptide derivatives of the invention may be modified for specific labeling and non-specific labeling of blood components.

A. Specific Labeling

Preferably, the modified angiogenic peptides of this invention are designed to specifically react with thiol groups on mobile blood proteins. Such reaction is preferably established by covalent bonding of a anti-angiogenic peptide modified with a maleimide link (e.g. prepared from GMBS, MPA or other maleimides) to a thiol group on a mobile blood protein such as serum albumin or IgG.

Under certain circumstances, specific labeling with maleimides (maleimido groups) offers several advantages over non-specific labeling of mobile proteins with groups such as NHS and sulfo-NHS. Thiol groups are less abundant in vivo than amino groups. Therefore, the maleimide derivatives of this invention will covalently bond to fewer proteins. For example, in albumin (the most abundant blood protein) there is only a single thiol group. Thus, peptide-maleimide-albumin conjugates will tend to comprise approximately a 1:1 molar ratio of peptide to albumin. In addition to albumin, IgG molecules (class II) also have free thiols. Since IgG molecules and serum albumin make up the majority of the soluble protein in blood they also make up the majority of the free thiol groups in blood that are available to covalently bond to maleimide-modified peptides.

Further, even among free thiol-containing blood proteins, specific labeling with maleimides leads to the preferential formation of peptide-maleimide-albumin conjugates, due to the unique characteristics of albumin itself. The single free thiol group of albumin, highly conserved among species, is located at amino acid residue 34 ($Cys^{34}$). It has been demonstrated recently that the $Cys^{34}$ of albumin has increased reactivity relative to free thiols on other free thiol-containing proteins. This is due in part to the very low pK value of 5.5 for the $Cys^{34}$ of albumin. This is much lower than typical pK values for cysteines residues in general, which are typically about 8. Due to this low pK, under normal physiological conditions $Cys^{34}$ of albumin is predominantly in the ionized form, which dramatically increases its reactivity. In addition to the low pK value of $Cys^{34}$, another factor which enhances the reactivity of $Cys^{34}$ is its location, which is in a crevice close to the surface of one loop of region V of albumin. This location makes $Cys^{34}$ very available to ligands of all kinds, and is an important factor in $Cys^{34}$'s biological role as free radical trap and free thiol scavenger. These properties make $Cys^{34}$ highly reactive with maleimide peptides, and the reaction rate acceleration can be as much as 1000-fold relative to rates of reaction of maleimide peptides with other free-thiol containing proteins.

Another advantage of peptide-maleimide-albumin conjugates is the reproducibility associated with the 1:1 loading of peptide to albumin specifically at $Cys^{34}$. Other techniques, such as glutaraldehyde, DCC, EDC and other chemical activations of, for example, free amines lack this selectivity. For example, albumin contains 52 lysine residues, 25-30 of which are located on the surface of albumin and accessible for conjugation. Activating these lysine residues, or alternatively modifying peptides to couple through these lysine residues, results in a heterogenous population of conjugates. Even if 1:1 molar ratios of peptide to albumin are employed, the yield will consist of multiple conjugation products, some containing 0, 1, 2 or more peptides per albumin, and each having peptides randomly coupled at any one of the 25-30 available lysine sites. Given the numerous combinations possible, characterization of the exact composition and nature of each batch becomes difficult, and batch-to-batch reproducibility is all but impossible, making such conjugates less desirable as anti-angiogenic peptides. Additionally, while it would seem that conjugation through lysine residues of albumin would at least have the advantage of delivering more anti-angiogenic agent per albumin molecule, studies have shown that a 1:1 ratio of anti-angiogenic agent to albumin is preferred. In an article by Stehle, et al., "The Loading Rate Determines Tumor Targeting Properties of Methotrexate-Albumin Conjugates in Rats," *Anti-Cancer Drugs*, Vol. 8, pp. 677-685 (1997), incorporated herein in its entirety, the authors report that a 1:1 ratio of the anti-cancer methotrexate to albumin conjugated via glutaraldehyde gave the most promising results. These conjugates were taken up by tumor cells, whereas conjugates bearing 5:1 to 20:1 methotrexate molecules had altered HPLC profiles and were quickly taken up by the liver in vivo. It is postulated that at these higher ratios, conformational changes to albumin diminish its effectiveness as a therapeutic carrier.

Through controlled administration of maleimide-peptides in vivo, one can control the specific labeling of albumin and IgG in vivo. In typical administrations, 80-90% of the administered maleimide-peptides will label albumin and less than 5% will label IgG. Trace labeling of free thiols such as glutathione will also occur. Such specific labeling is preferred for in vivo use as it permits an accurate calculation of the estimated half-life of the administered agent.

In addition to providing controlled specific in vivo labeling, maleimide-peptides can provide specific labeling of serum albumin and IgG ex vivo. Such ex vivo labeling involves the addition of maleimide-peptides to blood, serum or saline solution containing serum albumin and/or IgG. Once modified ex vivo with maleimide-peptides, the blood, serum or saline solution can be readministered to the blood for in vivo treatment.

In contrast to NHS-peptides, maleimide-peptides are generally quite stable in the presence of aqueous solutions and in the presence of free amines. Since maleimide-peptides will only react with free thiols, protective groups are generally not necessary to prevent the maleimide-peptides from reacting with itself. In addition, the increased stability of the peptide permits the use of further purification steps such as HPLC to prepare highly purified products suitable for in vivo use. Lastly, the increased chemical stability provides a product with a longer shelf life.

B. Non-Specific Labeling.

The kringle 5 peptides of the invention may also be modified for non-specific labeling of blood components. Bonds to amino groups will also be employed, particularly with the formation of amide bonds for non-specific labeling. To form such bonds, one may use as a chemically reactive group coupled to the kringle 5 peptide a wide variety of active carboxyl groups, particularly esters, where the hydroxyl moiety is physiologically acceptable at the levels required. While a number of different hydroxyl groups may be employed in these linking agents, the most convenient would be N-hydroxysuccinimide (NHS) and N-hydroxy-sulfosuccinimide (sulfo-NHS), which form succinimidyl groups.

Other linking agents which may be utilized are described in U.S. Pat. No. 5,612,034, which is hereby incorporated herein.

The various sites with which the chemically reactive group of the subject non-specific kringle 5 peptide derivatives may react in vivo include cells, particularly red blood cells (erythrocytes) and platelets, and proteins, such as immunoglobulins, including IgG and IgM, serum albumin, ferritin, steroid binding proteins, transferrin, thyroxin binding protein, α-2-macroglobulin, and the like. Those receptors with which the derivatized kringle 5 peptides react, which are not long-lived, will generally be eliminated from the human host within about three days. The proteins indicated above (including the proteins of the cells) will remain at least three days, and may remain five days or more (usually not exceeding 60 days, more usually not exceeding 30 days) particularly as to the half life, based on the concentration in the blood.

For the most part, reaction will be with mobile components in the blood, particularly blood proteins and cells, more particularly blood proteins and erythrocytes. By "mobile" is intended that the component does not have a fixed situs for any extended period of time, generally not exceeding 5, more usually one minute, although some of the blood component may be relatively stationary for extended periods of time. Initially, there will be a relatively heterogeneous population of functionalized proteins and cells. However, for the most part, the population within a few days will vary substantially from the initial population, depending upon the half-life of the functionalized proteins in the blood stream. Therefore, usually within about three days or more, IgG will become the predominant functionalized protein in the blood stream.

Usually, by day 5 post-administration, IgG, serum albumin and erythrocytes will be at least about 60 mole %, usually at least about 75 mole %, of the conjugated components in blood, with IgG, IgM (to a substantially lesser extent) and serum albumin being at least about 50 mole %, usually at least about 75 mole %, more usually at least about 80 mole %, of the non-cellular conjugated components.

Preferably, the kringle 5 peptide derivative is conjugated to albumin.

The desired conjugates of non-specific kringle 5 peptides to blood components may be prepared in vivo by administration of the kringle 5 peptide derivatives to the patient, which may be a human or other mammal. The administration may be done in the form of a bolus or introduced slowly over time by infusion using metered flow or the like.

If desired, the subject conjugates may also be prepared ex vivo by combining blood with derivatized kringle 5 peptides of the present invention, allowing covalent bonding of the derivatized kringle 5 peptides to reactive functionalities on blood components and then returning or administering the conjugated blood to the host. Moreover, the above may also be accomplished by first purifying an individual blood component or limited number of components, such as red blood cells, immunoglobulins, serum albumin, or the like, and combining the component or components ex vivo with the chemically reactive kringle 5 peptide derivatives. The functionalized blood or blood component may then be returned to the host to provide in vivo the subject therapeutically effective conjugates. The blood also may be treated to prevent coagulation during handling ex vivo.

3. Synthesis of Modified Kringle 5 Peptides

A. Kringle 5 Peptide Synthesis

Kringle 5 peptide fragments may be synthesized by standard methods of solid phase peptide chemistry known to those of ordinary skill in the art. For example, kringle 5 peptide fragments may be synthesized by solid phase chemistry techniques following the procedures described by Steward and Young (Steward, J. M. and Young, J. D., Solid Phase Peptide Synthesis, 2nd Ed., Pierce Chemical Company, Rockford, Ill., (1984) using an Applied Biosystem synthesizer. Similarly, multiple fragments may be synthesized then linked together to form larger fragments. These synthetic peptide fragments can also be made with amino acid substitutions at specific locations.

For solid phase peptide synthesis, a summary of the many techniques may be found in J. M. Stewart and J. D. Young, Solid Phase Peptide Synthesis, W.H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, Vol. 1, Acacemic Press (New York). In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid is then either attached to an inert solid support or utilized in solution by adding the next amino acid in the sequence having the complimentary (amino or carboxyl) group suitably protected and under conditions suitable for forming the amide linkage. The protecting group is then removed from this newly added amino acid residue and the next amino acid (suitably protected) is added, and so forth.

After all the desired amino acids have been linked in the proper sequence, any remaining protecting groups (and any solid support) are removed sequentially or concurrently to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α, α-dimethyl-3,5-dimethoxybenzyloxycarbonyl, o-nitrophenylsulfenyl, 2-cyano-t-butyloxycarbonyl, and the like. The 9-fluorenyl-methyloxycarbonyl (Fmoc) protecting group is particularly preferred for the synthesis of kringle 5 peptide fragments. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxycarbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. The preferred solid support for synthesis of α-C-terminal carboxy peptides is 4-hydroxymethylphenoxymethyl-copoly(styrene-1% divinylbenzene). The preferred solid support for α-C-terminal amide peptides is the 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours at a temperature of between 10° and 50° C. in a solvent such as dichloromethane or DMF.

When the solid support is 4-(2',4'-dimethoxyphenyl-Fmoc-aminomethyl) phenoxy-acetamidoethyl resin, the Fmoc group is cleaved with a secondary amine, preferably piperidine, prior to coupling with the α-C-terminal amino acid as described above. The preferred method for coupling to the deprotected 4-(2',4'-dimethoxyphenyl-Fmoc-aminomethyl)phenoxy-acetamidoethyl resin is O-benzotriazol-1-yl-N,N,N',N'-tetramethyluroniumhexafluoro-phosphate (HBTU, 1 equiv.) and 1-hydroxybenzotriazole (HOBT, 1 equiv.) in DMF. The coupling of successive protected amino acids can be carried out in an automatic polypeptide synthesizer as is well known in the art. In a preferred embodiment, the α-N-terminal amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent is normally O-benzotriazol-1-yl-N,N,N',N'-tetramethyluroniumhexafluoro-phosphate (HBTU, 1 equiv.) and 1-hydroxybenzotriazole (HOBT, 1 equiv.).

At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage cocktail described above. The fully deprotected peptide is purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Molecular weights of these kringle 5 peptides are determined using Fast Atom Bombardment (FAB) Mass Spectroscopy.

The kringle 5 peptides of the invention may be synthesized with N- and C-terminal protecting groups.

1. N-Terminal Protective Groups.

The term "N-protecting group" refers to those groups intended to protect the α-N-terminal of an amino acid or peptide or to otherwise protect the amino group of an amino acid or peptide against undesirable reactions during synthetic procedures. Commonly used N-protecting groups are disclosed in Greene, "Protective Groups In Organic Synthesis," (John Wiley & Sons, New York (1981)), which is hereby incorporated by reference. Additionally, protecting groups can be used as pro-drugs which are readily cleaved in vivo, for example, by enzymatic hydrolysis, to release the biologically active parent. α-N-protecting groups comprise loweralkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl, 9-fluorenylmethyloxycarbonyl (Fmoc) and the like and silyl groups such as trimethylsilyl and the like.

Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz). For example, lysine may be protected at the α-N-terminal by an acid labile group (e.g. Boc) and protected at the α-N-terminal by a base labile group (e.g. Fmoc) then deprotected selectively during synthesis.

2. Carboxyl Protective Groups.

The term "carboxyl protecting group" refers to a carboxylic acid protecting ester or amide group employed to block or protect the carboxylic acid functionality while the reactions involving other functional sites of the compound are performed. Carboxy protecting groups are disclosed in Greene, "Protective Groups in Organic Synthesis" pp. 152-186 (1981), which is hereby incorporated by reference. Additionally, a carboxy protecting group can be used as a pro-drug whereby the carboxy protecting group can be readily cleaved in vivo, for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated herein by reference. Representative carboxy protecting groups are $C_1$-$C_8$ loweralkyl (e.g., methyl, ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereofsuch as 5-indanyl and the like; dialkylaminoalkyl such as dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyl, benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonylmethyl, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl such as 2-(phenoxycarbonyloxy)ethyl, 2-(5-indanyloxycarbonyloxy)ethyl and the like; alkoxyalkylcarbonyloxyalkyl such as 2-(1-methoxy-2-methylpropan-2-oyloxy)ethyl and like; arylalkyloxycarbonyloxyalkyl such as 2-(benzyloxycarbonyloxy)ethyl and the like; arylalkenyloxycarbonyloxyalkyl such as 2-(3-phenylpropen-2-yloxycarbonyloxy)ethyl and the like; alkoxycarbonylaminoalkyl such as t-butyloxycarbonylaminomethyl and the like; alkylaminocarbonylaminoalkyl such as methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonylmethyl and the like; (5-(loweralkyl)-2-oxo-1,3-dioxolen-4-yl)alkyl such as (5-t-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like.

Representative amide carboxy protecting groups are aminocarbonyl and loweralkylaminocarbonyl groups.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester. Preferred amide carboxy protecting groups are loweralkylaminocarbonyl groups. For example, aspartic acid may be protected at the α-C-terminal by an acid labile group (e.g. t-butyl) and protected at the β-C-terminal by a hydrogenation labile group (e.g. benzyl) then deprotected selectively during synthesis.

B. Modification of Kringle 5 Peptides

The manner of producing the modified kringle 5 peptides of the present invention will vary widely, depending upon the nature of the various elements comprising the molecule. The synthetic procedures will be selected so as to be simple, provide for high yields, and allow for a highly purified product. Normally, the chemically reactive group will be created at the last stage, for example, with a carboxyl group, esterification to form an active ester will be the last step of the synthesis. Specific methods for the production of derivatized kringle 5 peptides of the present invention are described in examples below.

Each kringle 5 peptide selected to undergo the derivatization with a linker and a reactive agent will be modified according to the following criteria: if a carboxylic group, not critical for the retention of pharmacological activity is available on the original molecule and no other reactive functionality is present on the molecule, then the carboxylic acid will be chosen as attachment point for the linker-reactive group modification. If no carboxylic acids are available, then any other functionalities not critical for the retention of pharmacological activity will be selected as attachment point for the linker-reactive group modification. If several functionalities are available on kringle 5 peptide, a combination of protecting groups will be used in such a way that after addition of the linker/reactive group and deprotection of all the protected functional groups, retention of pharmacological activity is still obtained. If no reactive functionalities are available on the therapeutic agent, synthetic efforts will allow for a modification of the original parent drug in such a way that retention of biological activity and retention of receptor or target specificity is obtained.

The chemically reactive group is at a site, so that when the peptide is bonded to the blood component, the peptide retains a substantial proportion of the parent compound's inhibitor activity.

Even more specifically, each kringle 5 peptide selected to undergo the derivatization with a linker and a reactive group will be modified according to the following criteria: if a terminal carboxylic group is available on the kringle 5 peptide and is not critical for the retention of pharmacological activity, and no other sensitive functional group is present on the kringle 5 peptide, then the carboxylic acid will be chosen as attachment point for the linker-reactive group modification. If the terminal carboxylic group is involved in pharmacological activity, or if no carboxylic acids are available, then any other sensitive functional group not critical for the retention of pharmacological activity will be selected as the attachment point for the linker-reactive group modification. If several sensitive functional groups are available on a kringle 5 peptide, a combination of protecting groups will be used in such a way that after addition of the linker/reactive entity and deprotection of all the protected sensitive functional groups, retention of pharmacological activity is still obtained. If no sensitive functional groups are available on the therapeutic peptide, [or if a simpler modification route is desired], synthetic efforts will allow for a modification of the original kringle 5 peptide in such a way that retention of biological activity and retention of receptor or target specificity is obtained. In this case the modification will occur at the opposite end of the peptide.

An NHS derivative may be synthesized from a carboxylic acid in absence of other sensitive functional groups in the kringle 5 peptide. Specifically, such a kringle 5 peptide is reacted with N-hydroxysuccinimide in anhydrous $CH_2Cl_2$ and EDC, and the product is purified by chromatography or recrystallized from the appropriate solvent system to give the NHS derivative.

Alternatively, an NHS derivative may be synthesized from a kringle 5 peptide that contains an amino and/or thiol group and a carboxylic acid. When a free amino or thiol group is present in the molecule, it is preferable to protect these sensitive functional groups prior to perform the addition of the NHS derivative. For instance, if the molecule contains a free amino group, a transformation of the amine into a Fmoc or preferably into a tBoc protected amine is necessary prior to perform the chemistry described above. The amine functionality will not be deprotected after preparation of the NHS derivative. Therefore this method applies only to a peptide whose amine group is not required to be freed to induce a pharmacological desired effect.

In addition, an NHS derivative may be synthesized from a kringle 5 peptide containing an amino or a thiol group and no carboxylic acid. When the selected molecule contains no carboxylic acid, an array of bifunctional linkers can be used to convert the molecule into a reactive NHS derivative. For instance, ethylene glycol-bis(succinimydylsuccinate) (EGS) and triethylamine dissolved in DMF and added to the free amino containing molecule (with a ratio of 10:1 in favor of EGS) will produce the mono NHS derivative. To produce an NHS derivative from a thiol derivatized molecule, one can use N-[γ-maleimidobutyryloxy]succinimide ester (GMBS) and triethylamine in DMF. The maleimido group will react with the free thiol and the NHS derivative will be purified from the reaction mixture by chromatography on silica or by HPLC.

An NHS derivative may also be synthesized from a kringle 5 peptide containing multiple sensitive functional groups. Each case is have to be analyzed and solved in a different manner. However, thanks to the large array of protecting groups and bifunctional linkers that are commercially available, as described above, this invention is applicable to any peptide with preferably one chemical step only to derivatize the peptide or two steps by first protecting a sensitive group or three steps (protection, activation and deprotection). Under exceptional circumstances only, would one require to use multiple steps (beyond three steps) synthesis to transform a kringle 5 peptide into an active NHS or maleimide derivative.

A maleimide derivative may also be synthesized from a kringle 5 peptide containing a free amino group and a free carboxylic acid. To produce a maleimide derivative from a amino derivatized molecule, one can use N-[γ-maleimidobutyryloxy]succinimide ester (GMBS) and triethylamine in DMF. The succinimide ester group will react with the free amino and the maleimide derivative will be purified from the reaction mixture by crystallization or by chromatography on silica or by HPLC.

Finally, a maleimide derivative may be synthesized from a kringle 5 peptide containing multiple other sensitive functional groups and no free carboxylic acids. When the selected molecule contains no carboxylic acid, an array of bifunctional crosslinking reagents can be used to convert the molecule into a reactive NHS derivative. For instance maleimidopropionic acid (MPA) can be coupled to the free amine to produce a maleimide derivative through reaction of the free amine with the carboxylic group of MPA using HBTU/HOBt/DIEA activation in DMF.

A large number of bifunctional compounds are available for linking to entities. Illustrative entities include: azidobenzoyl hydrazide, N-[4-(p-azidosalicylamino)butyl]-3'-[2'-pyridydithio)propionamide), bis-sulfosuccinimidyl suberate, dimethyl adipimidate, disuccinimidyl tartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate; glutaraldehyde, and succinimidyl 4-[N-maleimidomethyl]cyclohexane-1-carboxylate.

4. Uses of the Modified Kringle 5 Peptides

As described earlier, angiogenesis includes a variety of processes involving neovascularization of a tissue including "sprouting", vasculogenesis, or vessel enlargement. With the exception of traumatic wound healing, corpus leuteum formation and embryogenesis, it is believed that the majority of angiogenesis processes are associated with disease processes and therefore the use of the present therapeutic methods are selective for the disease and do not have deleterious side effects.

There are a variety of diseases in which angiogenesis is believed to be important, which may be treatable with the modified peptides of the invention. These diseases include, but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth.

The modified kringle 5 peptides of the invention find use in methods which inhibit angiogenesis in a diseased tissue ameliorates symptoms of the disease and, depending upon the disease, can contribute to cure of the disease. The modified peptides of the invention are more stable in vivo and, as such, smaller amounts of the modified peptide can be administered for effective treatment In one embodiment, the invention contemplates inhibition of angiogenesis, per se, in a tissue. The extent of angiogenesis in a tissue, and therefore the extent of inhibition achieved by the present methods, can be evaluated by a variety of method, for detecting $\alpha_5B_3$-immunopositive immature and nascent vessel structures by immunohistochemistry.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

In one related embodiment, a tissue to be treated with the modified kringle 5 peptides of the invention is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated in the present invention in its many embodiments is desirably a human patient, although it is to be understood that the principles of the invention indicate that the invention is effective with respect to all mammals, which are intended to be included in the term "patient." In this context, a mammal is understood to include any mammalian species in which treatment of diseases associated with angiogenesis is desirable, particularly agricultural and domestic mammalian species.

In another related embodiment, a tissue to be treated with the modified kringle 5 peptides of the invention is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated with the modified kringle 5 peptides of the invention is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, and the like tissues.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

The present invention thus provides for a method of inhibiting tumor neovascularization by inhibiting tumor angiogenesis according to the present methods using the modified kringle 5 peptides of the invention. Similarly, the invention provides a method of inhibiting tumor growth by practicing the angiogenesis-inhibiting methods. The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of the modified kringle 5 peptides of the invention is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the modified kringle 5 peptides after surgery where solid tumors have been removed as a prophylaxis against metastases. Insofar as the present methods apply to inhibition of tumor neovascularization, the methods can also apply to inhibition of tumor tissue growth, to inhibition of tumor metastases formation, and to regression of established tumors using the modified kringle 5 peptides of the invention.

Restenosis is a process of smooth muscle cell (SMC) migration and proliferation at the site of percutaneous transluminal coronary angioplasty which hampers the success of angioplasty. The migration and proliferation of SMC's during restenosis can be considered a process of angiogenesis which is inhibited by the modified kringle 5 peptides of the present invention. Therefore, the invention also contemplates inhibition of restenosis by inhibiting angiogenesis in a patient following angioplasty procedures. For inhibition of restenosis, the modified kringle 5 peptide is typically administered after the angioplasty procedure for from about 2 to about 28 days, and more typically for about the first 14 days following the procedure.

The present method for inhibiting angiogenesis in a tissue comprises contacting a tissue in which angiogenesis is occurring, or is at risk for occurring, with a composition comprising a therapeutically effective amount of a modified kringle 5 peptide. The dosage ranges for the administration of the modified kringle 5 peptide depend upon the form of the peptide, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

As angiogenesis inhibitors, such modified kringle 5 peptides are useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas; prophylaxis of autoimmune diseases including rheumatoid, immune and degenerative arthritis; ocular diseases including diabetic retinopathy, retinopathy of prematurity, corneal graft rejection, retrolental fibroplasia, neovascular glaucoma, rubeosis, retinal neovascularization due to macular degeneration and hypoxia; abnormal neovascularization conditions of the eye; skin diseases including psoriasis; blood vessel diseases including hemagiomas and capillary proliferation within atherosclerotic plaques; Osler-Webber Syndrome; myocardial angiogenesis; plaque neovascularization; telangiectasia; hemophiliac joints; angiofibroma; wound granulation; diseases characterized by excessive or abnormal stimulation of endothelial cells including intestinal adhesions, Crohn's disease, atherosclerosis, scleroderma and hypertrophic scars (i.e. keloids) and diseases which have angiogenesis as a pathologic consequence including cat scratch disease (*Rochele minalia* quintosa) and ulcers (*Helicobacter pylori*). Another use is as a birth control agent which inhibits ovulation and establishment of the placenta.

The modified kringle 5 peptides of the present invention may also be useful for the prevention of metastases from the tumors described above either when used alone or in combination with radiotherapy and/or other chemotherapeutic treatments conventionally administered to patients for treating angiogenic diseases. For example, when used in the treatment of solid tumors, the modified kringle 5 peptides of the present invention may be administered with chemotherapeutic agents such as alpha inteferon, COMP (cyclophosphamide, vincristine, methotrexate and prednisone), etoposide, mBACOD (methortrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogs including methotrexate; pyrimidine analogues including 5-fluorouracil, cytosine arabinoside; purine analogs including 6-mercaptopurine and 6-thioguanine; antitumor antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar. For example, a tumor may be treated conventionally with surgery, radiation or chemotherapy and kringle 5 administration with subsequent kringle 5 administration to extend the dormancy of micrometastases and to stabilize and inhibit the growth of any residual primary tumor.

5. Administration of the Modified Kringle 5 Peptides

The modified kringle 5 peptides will be administered in a physiologically acceptable medium, e.g. deionized water, phosphate buffered saline (PBS), saline, aqueous ethanol or other alcohol, plasma, proteinaceous solutions, mannitol, aqueous glucose, alcohol, vegetable oil, or the like. Other additives which may be included include buffers, where the media are generally buffered at a pH in the range of about 5 to 10, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The subject modified kringle 5 peptides will for the most part be administered orally, parenterally, such as intravascularly (IV), intraarterially (IA), intramuscularly (IM), subcutaneously (SC), or the like. Administration may in appropriate situations be by transfusion. In some instances, where reaction of the functional group is relatively slow, administration may be oral, nasal, rectal, transdermal or aerosol, where the nature of the conjugate allows for transfer to the vascular system. Usually a single injection will be employed although more than one injection may be used, if desired. The modified kringle 5 peptides may be administered by any convenient means, including syringe, trocar, catheter, or the like. The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g., intravenously, peripheral or central vein. Other routes may find use where the administration is coupled with slow release techniques or a protective matrix. The intent is that the kringle 5 peptide, analog or derivative be effectively distributed in the blood, so as to be able to react with the blood components. The concentration of the conjugate will vary widely, generally ranging from about 1 pg/ml to 50 mg/ml. The total administered intravascularly will generally be in the range of about 0.1 mg/ml to about 10 mg/ml, more usually about 1 mg/ml to about 5 mg/ml.

By bonding to long-lived components of the blood, such as immunoglobulin, serum albumin, red blood cells and platelets, a number of advantages ensue. The activity of the modified kringle 5 peptide compound is extended for days to weeks. Only one administration need be given during this period of time. Greater specificity can be achieved, since the active compound will be primarily bound to large molecules, where it is less likely to be taken up intracellularly to interfere with other physiological processes.

The formation of the covalent bond between the blood component may occur in vivo or ex vivo. For ex vivo covalent bond formation the modified kringle 5 peptide is added to blood, serum or saline solution containing human serum albumin or IgG to permit covalent bond formation between the modified kringle 5 peptide and the blood component. In a preferred format, the kringle 5 peptide is modified with maleimide and it is reacted with human serum albumin in saline solution. Once the modified kringle 5 peptide has reacted with the blood component, to form a kringle 5 peptide-protein conjugate, the conjugate may be administered to the patient.

Alternatively, the modified kringle 5 peptide may be administered to the patient directly so that the covalent bond forms between the modified kringle 5 peptide and the blood component in vivo.

6. Monitoring the Presence of Modified Kringle 5 Peptide

The blood of the mammalian host may be monitored for the presence of the modified kringle 5 peptide compounds one or more times. By taking a portion or sample of the blood of the host, one may determine whether the kringle 5 peptide has become bound to the long-lived blood components in sufficient amount to be therapeutically active and, thereafter, the level of kringle 5 peptide compound in the blood. If desired, one may also determine to which of the blood components the kringle 5 peptide derivative molecule is bound. This is particularly important when using non-specific kringle 5 peptides. For specific maleimide-kringle 5 peptides, it is much simpler to calculate the half life of serum albumin and IgG.

The modified kringle 5 peptides may be monitored using HPLC-MS or antibodies directed to kringle 5 peptides.

A. HPLC-MS

HPLC coupled with mass spectrometry (MS) can be utilized to assay for the presence of peptides and modified peptides as is well known to the skilled artisan. Typically two mobile phases are utilized: 0.1% TFA/water and 0.1% TFA/acetonitrile. Column temperatures can be varied as well as gradient conditions. Particular details are outlined in the Examples section below.

B. Antibodies

Another aspect of this invention relates to methods for determining the concentration of the kringle 5 peptides and/or analogs, or their derivatives and conjugates in biological samples (such as blood) using antibodies specific to the kringle 5 peptides or peptide analogs or their derivatives and conjugates, and to the use of such antibodies as a treatment for toxicity potentially associated with such kringle 5 peptides and/or their derivatives or conjugates. This is advantageous because the increased stability and life of the kringle 5 peptides in vivo in the patient might lead to novel problems during treatment, including increased possibility for toxicity. The use of anti-therapeutic agent antibodies, either monoclonal or polyclonal, having specificity for a particular kringle 5 peptides, can assist in mediating any such problem. The antibody may be generated or derived from a host immunized with the particular modified kringle 5 peptide, or with an immunogenic fragment of the agent, or a synthesized immunogen corresponding to an antigenic determinant of the agent. Preferred antibodies will have high specificity and affinity for native, derivatized and conjugated forms of the modified kringle 5 peptide. Such antibodies can also be labeled with enzymes, fluorochromes, or radiolables.

Antibodies specific for modified kringle 5 peptides may be produced by using purified kringle 5 peptides for the induction of derivatized kringle 5 peptide-specific antibodies. By induction of antibodies, it is intended not only the stimulation of an immune response by injection into animals, but analogous steps in the production of synthetic antibodies or other specific binding molecules such as screening of recombinant immunoglobulin libraries. Both monoclonal and polyclonal antibodies can be produced by procedures well known in the art.

The antibodies may be used to monitore the presence of kringle 5 petides in the blood stream. Blood and/or serum samples may be analyzed by SDS-PAGE and western blotting. Such techniques permit the analysis of the blood or serum to determine the bonding of the modified kringle 5 peptides to blood components.

The anti-therapeutic agent antibodies may also be used to treat toxicity induced by administration of the modified kringle 5 peptide, and may be used ex vivo or in vivo. Ex vivo methods would include immuno-dialysis treatment for toxicity employing anti-therapeutic agent antibodies fixed to solid supports. In vivo methods include administration of anti-therapeutic agent antibodies in amounts effective to induce clearance of antibody-agent complexes.

The antibodies may be used to remove the modified kringle 5 peptides and conjugates thereof, from a patient's blood ex vivo by contacting the blood with the antibodies under sterile conditions. For example, the antibodies can be fixed or otherwise immobilized on a column matrix and the patient's blood can be removed from the patient and passed over the matrix. The modified kringle 5 peptides will bind to the antibodies and the blood containing a low concentration of the kringle 5 peptide, then may be returned to the patient's circulatory system. The amount of modified kringle 5 peptide removed can be controlled by adjusting the pressure and flow rate. Preferential removal of the modified kringle 5 peptides from the plasma component of a patient's blood can be effected, for example, by the use of a semipermeable membrane, or by otherwise first separating the plasma component from the cellular component by ways known in the art prior to passing the plasma component over a matrix containing the anti-therapeutic antibodies. Alternatively the preferential removal of kringle 5 peptide—conjugated blood cells, including red blood cells, can be effected by collecting and concentrating the blood cells in the patient's blood and contacting those cells with fixed anti-therapeutic antibodies to the exclusion of the serum component of the patient's blood.

The anti-therapeutic antibodies can be administered in vivo, parenterally, to a patient that has received the modified kringle 5 peptide or conjugates for treatment. The antibodies will bind the kringle 5 peptide compounds and conjugates. Once bound the kringle 5 peptide activity will be hindered if not completely blocked thereby reducing the biologically effective concentration of kringle 5 peptide compound in the patient's bloodstream and minimizing harmful side effects. In addition, the bound antibody—kringle 5 peptide complex will facilitate clearance of the kringle 5 peptide compounds and conjugates from the patient's blood stream.

The invention having been fully described is now exemplified by the following non-limiting examples.

EXAMPLES

General

Solid phase peptide synthesis of the Kringle-5 analogs on a 100 µmole scale was performed using manual solid-phase synthesis and a Symphony Peptide Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1). When required, the selective deprotection of the Lys (Aloc) group was performed manually and accomplished by treating the resin with a solution of 3 eq of $Pd(PPh_3)_4$ dissolved in 5 mL of $CHCl_3$:NMM:HOAc (18:1:0.5) for 2 h (Step 2). The resin was then washed with $CHCl_3$ (6×5 mL), 20% HOAc in DCM (6×5 mL), DCM (6×5 mL), and DMF (6×5 mL). In some instances, the synthesis was then re-automated for the addition of one AEEA (aminoethoxy-ethoxyacetic acid) group, the addition of acetic acid or the addition of a 3-maleimidopropionic acid (MPA) (Step 3). Resin cleavage and product isolation was performed using 85% TFA/5% TIS/5% thioanisole and 5% phenol, followed by precipitation by dry-ice cold $Et_2O$ (Step 4). The products were purified by preparative reverse phase HPLC using a Varian (Rainin) preparative binary HPLC system: gradient elution of 30-55% B (0.045% TFA in $H_2O$ (A) and 0.045% TFA in $CH_3CN$ (B)) over 180 min at 9.5 mL/min using a Phenomenex Luna 10µ phenyl-hexyl, 21 mm×25 cm column and UV detector (Varian Dynamax UVD II) at λ214 and 254 nm. Purity was determined 95% by RP-HPLC mass spectrometry using a Hewlett Packard LCMS-1100 series spectrometer equipped with a diode array detector and using electro-spray ionization.

Example 1

Preparation of NAc-Pro-Arg-Lys-Leu-Tyr-Asp-Lys-$NH_2$.3TFA

Using automated peptide synthesis, the following protected amino acids were sequentially added to Rink Amide MBHA resin: Fmoc-Lys(Boc)-OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH. Deblocking of the Fmoc group the N-terminal of the resin-bound amino acid was performed with 20% piperidine in DMF for about 15-20 minutes. Coupling of the acetic acid was performed under conditions similar to amino acid coupling. Final cleavage from the resin was performed using cleavage mixture as described above. The product was isolated by precipitation and purified by preparative HPLC to afford the desired product as a white solid upon lyophilization Example 2

Preparation of NAc-Arg-Lys-Leu-Tyr-Asp-Tyr-Lys-$NH_2$.3TFA

Using automated peptide synthesis, the following protected amino acids were sequentially added to Rink Amide MBHA resin: Fmoc-Lys(Boc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH. Deblocking of the Fmoc group the N-terminal of the resin-bound amino acid was performed with 20% piperidine in DMF for about 15-20 minutes. Coupling of the acetic acid was performed under conditions similar to amino acid coupling. Final cleavage from the resin was performed using cleavage mixture as described above. The product was isolated by precipitation and purified by preparative HPLC to afford the desired product as a white solid upon lyophilization.

Example 3

Preparation of Nac-Tyr-Thr-Thr-Asn-Pro-Arg-Lys-Leu-Tyr-Asp-Tyr-Lys-NH$_2$.3TFA

Using automated peptide synthesis, the following protected amino acids were sequentially added to Rink Amide MBHA resin: Fmoc-Lys(Boc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbo-OH, Fmoc-Pro-OH, Fmoc-Asn(Trt)-OH, Fmoc-Thr(tBu)-OH, Fmoc-Thr(tBu)-OH, Fmoc-Tyr(tBu)OH. Deblocking of the Fmoc group the N-terminal of the resin-bound amino acid was performed with 20% piperidine in DMF for about 15-20 minutes. Coupling of the acetic acid was performed under conditions similar to amino acid coupling. Final cleavage from the resin was performed using cleavage mixture as described above. The product was isolated by precipitation and purified by preparative HPLC to afford the desired product as a white solid upon lyophilization.

Example 4

Preparation of NAc-Arg-Asn-Pro-Asp-Gly-Asp-Val-Gly-Gly-Pro-Trp-Ala-Tyr-Thr-Thr-Asn-Pro-Arg-Lys-Leu-Tyr-Asp-Tyr-Lys-NH$_2$.4TFA Using automated peptide synthesis, the following protected amino acids were sequentially added to Rink Amide MBHA resin: Fmoc-Lys(Boc)-OH, Fmoc-Tyr(tBu)OH, Fmoc-Asp(OtBu)-OH, Fmoc-Tyr(tBu)OH, Fmoc-Leu-OH Fmoc-Lys(Boc)-OH, Fmoc-Arg(Pbf)-OH, Fmoc-Pro-OH, Fmoc-Asn(Trt)-OH, Fmoc-Thr(tBu)-OH, Fmoc-Thr(tBu)-OH, Fmoc-Tyr(tBu)OH, Fmoc-Ala-OH, Fmoc-Trp-OH, Fmoc-Pro-OH, Fmoc-Gly-OH, Fmoc-Gly-OH, Fmoc-Asp(OtBu)-OH, Fmoc-Gly-OH, Fmoc-Val-OH, Fmoc-Asp(OtBu)-OH, Fmoc-Pro-OH, Fmoc-Asn(Trt)-OH, Fmoc-Arg(Pbf)-OH. Deblocking of the Fmoc group the N-terminal of the resin-bound amino acid was performed with 20% piperidine in DMF for about 15-20 minutes. Coupling of the acetic acid was performed under conditions similar to amino acid coupling. Final cleavage from the resin was performed using cleavage mixture as described above. The product was isolated by precipitation and purified by preparative HPLC to afford the desired product as a white solid upon lyophilization.

Example 5

Preparation of NAc-Arg-Asn-Pro-Asp-Gly-Asp-Val-Gly-Gly-Pro-Trp-Lys-NH$_2$.2TFA

Using automated peptide synthesis, the following protected amino acids were sequentially added to Rink Amide MBHA resin: Fmoc-Lys(Boc)-OH, Fmoc-Trp-OH, Fmoc-Pro-OH, Fmoc-Gly-OH, Fmoc-Gly-OH, Fmoc-Val-OH, Fmoc-Asp(OtBu)-OH, Fmoc-Gly-OH, Fmoc-Asp(OtBu)-OH, Fmoc-Pro-OH, Fmoc-Asn(Trt)-OH, Fmoc-Arg(Pbf)-OH. Deblocking of the Fmoc group the N-terminal of the resin-bound amino acid was performed with 20% piperidine in DMF for about 15-20 minutes. Coupling of the acetic acid was performed under conditions similar to amino acid coupling. Final cleavage from the resin was performed using cleavage mixture as described above. The product was isolated by precipitation and purified by preparative HPLC to afford the desired product as a white solid upon lyophilization Example 6

Preparation of NAc-Pro-Arg-Lys-Leu-Tyr-Asp-Tyr-Lys-(Nε-MPA)-NH$_2$.2TFA

Using automated peptide synthesis, the following protected amino acids were sequentially added to Rink Amide MBHA resin: Fmoc-Lys(Aloc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH. Deblocking of the Fmoc group the N-terminal of the resin-bound amino acid was performed with 20% piperidine in DMF for about 15-20 minutes. Coupling of the acetic acid was performed under conditions similar to amino acid coupling. Final cleavage from the resin was performed using cleavage mixture as described above. The product was isolated by precipitation and purified by preparative HPLC to afford the desired product as a white solid upon lyophilization.

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reversed phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm.

Example 7

Preparation of (MPA-AEEA)-Pro-Arg-Lys-Leu-Tyr-Asp-Tyr-NH$_2$.2TFA

Solid phase peptide synthesis of the modified Kringle 5 peptide on a 100 μmole scale was performed on a Symphony Peptide Synthesizer using Fmoc protected Rink Amide MBHA resin, Fmoc protected amino acids, O-benzotriazol-1-yl-N, N, N',N'-tetramethyl-uronium hexafluorophosphate (HBTU) in N,N-dimethylformamide (DMF) solution and activation with N-methyl morpholine (NMM), and piperidine deprotection of Fmoc groups (Step 1).

Using automated peptide synthesis, the following protected amino acids were sequentially added to Rink Amide MBHA resin: Fmoc-Lys(Boc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH. The deprotection of the terminal Fmoc group is accomplished using 20% piperidine (Step 2) followed by the coupling of Fmoc-AEEA. Deprotection of the resulting Fmoc-AEEA-peptide with piperidine 20% in DMF allow for the subsequent addition of the 3-MPA (Step 3). Resin cleavage and product isolation was performed using 86% TFA/5% TIS/5% H$_2$O/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 µm, 21 mm×25 cm column equipped with a Dynamax C$_{18}$, 60 Å, 8 µm guard module, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 8

Preparation of (MPA)-Pro-Arg-Lys-Leu-Tyr-Asp-Tyr-NH$_2$.2TFA

Solid phase peptide synthesis of the modified Kringle 5 peptide on a 100 µmole scale was performed on a Symphony Peptide Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1). Using automated peptide synthesis, the following protected amino acids were sequentially added to Rink Amide MBHA resin: Fmoc-Lys(Boc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH. The deprotection of the terminal Fmoc group is accomplished using 20% piperidine (Step 2) followed by the coupling of 3-MPA (Step 3). Resin cleavage and product isolation was performed using 86% TFA/5% TIS/5% H$_2$O/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 µm, 21 mm×25 cm column equipped with a Dynamax C$_{18}$, 60 Å, 8 µm guard module, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 9

Preparation of NAc-Tyr-Th r-Thr-As n-Pro-Arg-Lys-Leu-Tyr-Asp-Tyr-Lys-(Nε-MPA)-NH$_2$.2TFA Using automated peptide synthesis, the following protected amino acids were sequentially added to Rink Amide MBHA resin: Fmoc-Lys(Aloc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH, Fmoc-Asn(Trt)-OH, Fmoc-Thr(tBu)-OH, Fmoc-Thr(tBu)-OH, Fmoc-Tyr(tBu)OH. Deblocking of the Fmoc group the N-terminal of the resin-bound amino acid was performed with 20% piperidine in DMF for about 15-20 minutes. Final cleavage from the resin was performed using cleavage mixture as described above. The product was isolated by precipitation and purified by preparative HPLC to afford the desired product as a white solid upon lyophilization The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm.

Example 10

5 Preparation of (MPA-AEEA)-Tyr-Thr-Thr-Asn-Pro-Arg-Lys-Leu-Tyr-Asp-Tyr-NH$_2$.2TFA Solid phase peptide synthesis of the modified Kringle 5 peptide on a 100 µmole scale was performed on a Symphony Peptide Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1).

Using automated peptide synthesis, the following protected amino acids were sequentially added to Rink Amide MBHA resin: Fmoc-Lys(Boc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf-OH, Fmoc-Pro-OH, Fmoc-Asn(Trt)-OH, Fmoc-Thr(tBu)-OH, Fmoc-Thr(tBu)-OH, Fmoc-Tyr(tBu)OH. The deprotection of the terminal Fmoc group is accomplished using 20% piperidine (Step 2) followed by the coupling of Fmoc-AEEA. Deprotection of the resulting Fmoc-AEEA-peptide with piperidine 20% in DMF allow for the subsequent addition of the 3-MPA (Step 3). Resin cleavage and product isolation was performed using 86% TFA/5% TIS/5% H$_2$O/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 µm, 21 mm×25 cm column equipped with a Dynamax C$_{18}$, 60 Å, 8 µm guard module, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 11

Preparation of (MPA)-Tyr-Thr-Thr-Asn-Pro-Arg-Lys-Leu-Tyr-Asp-Tyr-NH$_2$.2TFA

Solid phase peptide synthesis of the modified Kringle 5 peptide on a 100 µmole scale was performed on a Symphony Peptide Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1 Using automated peptide synthesis, the following protected amino acids were sequentially added to Rink Amide MBHA resin: Fmoc-Lys (Boc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH, Fmoc-Asn(Trt)-OH, Fmoc-Thr(tBu)-OH, Fmoc-Thr(tBu)-OH, Fmoc-Tyr(tBu) OH. The deprotection of the terminal Fmoc group is accomplished using 20% piperidine (Step 2) followed by the coupling of 3-MPA (Step 3). Resin cleavage and product isolation was performed using 86% TFA/5% TIS/5% $H_2O$/2% thioanisole and 2% phenol, followed by precipitation by dry-ice cold $Et_2O$ (Step 4). The product was purified by preparative reverse phase HPLC using a Varian (Rainin) preparative binary HPLC system using a Dynamax $C_{18}$, 60 Å, 8 μm, 21 mm×25 cm column equipped with a Dynamax $C_{18}$, 60 Å, 8 μm guard module, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 12

Preparation of NAc-Arg-Asn-Pro-Asp-Gly-Asp-Val-Gly-Gly-Pro-Trp-Ala-Tyr-Thr-Thr-Asn-Pro-Arg-Lys-Leu-Tyr-Asp-Tyr-Lys-($N_\epsilon$-MPA)-$NH_2$.3TFA Using automated peptide synthesis, the following protected amino acids were sequentially added to Rink Amide MBHA resin: Fmoc-Lys(Aloc)-OH, Fmoc-Tyr(tBu)OH, Fmoc-Asp(OtBu)-OH, Fmoc-Tyr(tBu)OH, Fmoc-Leu-OH Fmoc-Lys(Boc)-OH, Fmoc-Arg(Pbf-OH, Fmoc-Pro-OH, Fmoc-Asn(Trt)-OH, Fmoc-Thr(tBu)-OH, Fmoc-Thr(tBu)-OH, Fmoc-Tyr(tBu)OH, Fmoc-Ala-OH, Fmoc-Trp-OH, Fmoc-Pro-OH, Fmoc-Gly-OH, Fmoc-Gly-OH, Fmoc-Val-OH, Fmoc-Asp(OtBu)-OH, Fmoc-Gly-OH, Fmoc-Asp (OtBu)-OH, Fmoc-Pro-OH, Fmoc-Asn(Trt)-OH, Fmoc-Arg (Pbf)-OH. Deblocking of the Fmoc group the the N-terminal of the resin-bound amino acid was performed with 20% piperidine in DMF for about 15-20 minutes. Coupling of the acetic acid was performed under conditions similar to amino acid coupling. Final cleavage from the resin was performed using cleavage mixture as described above. The product was isolated by precipitation and purified by preparative HPLC to afford the desired product as a white solid upon lyophilization.

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2): The resin was then washed with CHCl$_3$ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10μ phenyl-hexyl, 21 mm×25 cm column and UV detector (Varian Dynamax UVD II) at λ214 and 254 nm.

Example 13

Preparation of (MPA-AEEA)-Arg-Asn-Pro-Asp-Gly-Asp-Val-Gly-Gly-Pro-Trp-Ala-Tyr-Thr-Thr-Asn-Pro-Arg-Lys-Leu-Tyr-Asp-Tyr-$NH_2$.3TFA Solid phase peptide synthesis of the modified Kringle 5 peptide on a 100 μmole scale was performed on a Symphony Peptide Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1).

Using automated peptide synthesis, the following protected amino acids were sequentially added to Rink Amide MBHA resin: Fmoc-Lys(Boc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH, Fmoc-Asn(Trt)-OH, Fmoc-Thr(tBu)-OH, Fmoc-Thr(tBu)-OH, Fmoc-Tyr(tBu)OH, Fmoc-Ala-OH, Fmoc-Trp-OH, Fmoc-Pro-OH, Fmoc-Gly-OH, Fmoc-Gly-OH, Fmoc-Val-OH, Fmoc-Asp(OtBu)-OH, Fmoc-Gly-OH, Fmoc-Asp (OtBu)-OH, Fmoc-Pro-OH, Fmoc-Asn(Trt)-OH, Fmoc-Arg (Pbf)-OH. The deprotection of the terminal Fmoc group is accomplished using 20% piperidine (Step 2) followed by the coupling of Fmoc-AEEA. Deprotection of the resulting Fmoc-AEEA-peptide with piperidine 20% in DMF allow for the subsequent addition of the 3-MPA (Step 3). Resin cleavage and product isolation was performed using 86% TFA/5% TIS/5% $H_2O$/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax $C_{18}$, 60 Å, 8 μm, 21 mm×25 cm column equipped with a Dynamax $C_{18}$, 60 Å, 8 μm guard module, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 14

Preparation of (MPA)-Arg-Asn-Pro-Asp-Gly-Asp-Val-Gly-Gly-Pro-Trp-Ala-Tyr-Thr-Thr-Asn-Pro-Arg-Lys-Leu-Tyr-Asp-Tyr-$NH_2$.3TFA Solid phase peptide synthesis of the modified Kringle 5 peptide on a 100 μmole scale was performed on a Symphony Peptide Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1). Using automated peptide synthesis, the following protected amino acids were sequentially added to Rink Amide MBHA resin: Fmoc-Lys (Boc)-OH, Fmoc-Tyr(tBu)OH, Fmoc-Asp(OtBu)-OH, Fmoc-Tyr(tBu)OH, Fmoc-Leu-OH Fmoc-Lys(Boc)-OH, Fmoc-Arg(Pbf)-OH, Fmoc-Pro-OH, Fmoc-Asn(Trt)-OH, Fmoc-Thr(tBu)-OH, Fmoc-Thr(tBu)-OH, Fmoc-Tyr(tBu) OH, Fmoc-Ala-OH, Fmoc-Trp-OH, Fmoc-Pro-OH, Fmoc-Gly-OH, Fmoc-Gly-OH, Fmoc-Asp(OtBu)-OH, Fmoc-Gly-OH, Fmoc-Val-OH, Fmoc-Asp(OtBu)-OH, Fmoc-Pro-OH, Fmoc-Asn(Trt)-OH, Fmoc-Arg(Pbf)-OH.

The deprotection of the terminal Fmoc group is accomplished using 20% piperidine (Step 2) followed by the coupling of 3-MPA (Step 3). Resin cleavage and product isolation was performed using 86% TFA/5% TIS/5% H$_2$O/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 µm, 21 mm×25 cm column equipped with a Dynamax C$_{18}$, 60 Å, 8 µm guard module, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 15

Preparation of NAc-Arg-Asn-Pro-Asp-Gly-Asp-Val-Gly-Gly-Pro-Trp-Lys-(N$_\epsilon$-MPA)-NH$_2$.TFA Solid phase peptide synthesis of the modified Kringle 5 peptide on a 100 µmole scale was performed on a Symphony Peptide Synthesizer using Fmoc protected Rink Amide MBHA resin, Fmoc protected amino acids, O-benzotriazol-1-yl-N, N, N',N'-tetramethyl-uronium hexafluorophosphate (HBTU) in N,N-dimethylformamide (DMF) solution and activation with N-methyl morpholine (NMM), and piperidine deprotection of Fmoc groups (Step 1).

Using automated peptide synthesis, the following protected amino acids were sequentially added to Rink Amide MBHA resin: Fmoc-Lys(Aloc)-OH, Fmoc-Trp-OH, Fmoc-Pro-OH, Fmoc-Gly-OH, Fmoc-Gly-OH, Fmoc-Val-OH, Fmoc-Asp(OtBu)-OH, Fmoc-Gly-OH, Fmoc-Asp(OtBu)-OH, Fmoc-Pro-OH, Fmoc-Asn(Trt)-OH, Fmoc-Arg(Pbf)-OH. The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm.

Example 16

5 Preparation of (MPA-AEEA)-Arg-Asn-Pro-Asp-Gly-Asp-Val-Gly-Gly-Pro-Trp-NH$_2$.TFA Solid phase peptide synthesis of the modified Kringle 5 peptide on a 100 µmole scale was performed on a Symphony Peptide Synthesizer using Fmoc protected Rink Amide MBHA resin, Fmoc protected amino acids, O-benzotriazol-1-yl-N, N, N',N'-tetramethyl-uronium hexafluorophosphate (HBTU) in N,N-dimethylformamide (DMF) solution and activation with N-methyl morpholine (NMM), and piperidine deprotection of Fmoc groups (Step 1).

Using automated peptide synthesis the following protected amino acids were sequentially added to Rink Amide MBHA resin: Fmoc-Lys(Boc)-OH, Fmoc-Trp-OH, Fmoc-Pro-OH, Fmoc-Gly-OH, Fmoc-Gly-OH, Fmoc-Asp(OtBu)-OH, Fmoc-Gly-OH, Fmoc-Val-OH, Fmoc-Asp(OtBu)-OH, Fmoc-Pro-OH, Fmoc-Asn(Trt)-OH, Fmoc-Arg(Pbf)-OH. The deprotection of the terminal Fmoc group is accomplished using 20% piperidine (Step 2) followed by the coupling of Fmoc-AEEA. Deprotection of the resulting Fmoc-AEEA-peptide with piperidine 20% in DMF allow for the subsequent addition of the 3-MPA (Step 3). Resin cleavage and product isolation was performed using 86% TFA/5% TIS/5% H$_2$O/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 µm, 21 mm×25 cm column equipped with a Dynamax C$_{18}$, 60 Å, 8 µm guard module, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 17

Preparation of (MPA)-Arg-Asn-Pro-Asp-Gly-Asp-Val-Gly-Gly-Pro-Trp-NH$_2$.TFA

Solid phase peptide synthesis of the modified Kringle 5 peptide on a 100 µmole scale was performed on a Symphony Peptide Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1). Using automated peptide synthesis, the following protected amino acids were sequentially added to Rink Amide MBHA resin: Fmoc-Lys (Boc)-OH, Fmoc-Trp-OH, Fmoc-Pro-OH, Fmoc-Gly-OH, Fmoc-Gly-OH, Fmoc-Asp(OtBu)-OH, Fmoc-Gly-OH, Fmoc-Val-OH, Fmoc-Asp(OtBu)-OH, Fmoc-Pro-OH, Fmoc-Asn(Trt)-OH, Fmoc-Arg(Pbf)-OH. The deprotection of the terminal Fmoc group is accomplished using 20% piperidine (Step 2) followed by the coupling of 3-MPA (Step 3). Resin cleavage and product isolation was performed using 86% TFA/5% TIS/5% H$_2$O/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 µm, 21 mm×25 cm column equipped with a Dynamax C$_{18}$, 60 Å, 8 µm guard module, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 18

Preparation of NAc-Arg-Lys-Leu-Tyr-Asp-Tyr-Lys-(Nε-MPA)-NH$_2$.2TFA

Using automated peptide synthesis, the following protected amino acids were sequentially added to Rink Amide MBHA resin: Fmoc-Lys(Aloc)-OH, Fmoc-Tyr(tBu)OH, Fmoc-Asp(OtBu)-OH, Fmoc-Tyr(tBu)OH, Fmoc-Leu-OH Fmoc-Lys(Boc)-OH, Fmoc-Arg(Pbf)-OH. Deblocking of the Fmoc group the the N-terminal of the resin-bound amino acid was performed with 20% piperidine in DMF for about 15-20 minutes. Coupling of the acetic acid was performed under conditions similar to amino acid coupling. Final cleavage from the resin was performed using cleavage mixture as described above. The product was isolated by precipitation and purified by preparative HPLC to afford the desired product as a white solid upon lyophilization. The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc 18:1: 0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm.

Example 19

Preparation of (MPA-AEEA)-Arg-Lys-Leu-Tyr-Asp-Tyr-NH$_2$.2TFA

Solid phase peptide synthesis of the modified Kringle 5 peptide on a 100 µmole scale was performed on a Symphony Peptide Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1).

Using automated peptide synthesis, the following protected amino acids were sequentially added to Rink Amide MBHA resin: Fmoc-Lys(Boc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH. The deprotection of the terminal Fmoc group is accomplished using 20% piperidine (Step 2) followed by the coupling of Fmoc-AEEA. Deprotection of the resulting Fmoc-AEEA-peptide with piperidine 20% in DMF allow for the subsequent addition of the 3-MPA (Step 3). Resin cleavage and product isolation was performed using 86% TFA/5% TIS/5% H$_2$O/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 µm, 21 mm×25 cm column equipped with a Dynamax C$_{18}$, 60 Å, 8 µm guard module, 21 mm×25 cm column and UV detector (Varian Dynamax UVD II) at λ214 and 254 nm.

The product had >95% purity as determined by RP-HPLC mass spectrometry using a Hewlett Packard LCMS-1100 series spectrometer equipped with a diode array detector and using electro-spray ionization Example 20

Preparation of (MPA)-Arg-Lys-Leu-Tyr-Asp-Tyr-NH$_2$.2TFA

Solid phase peptide synthesis of the modified Kringle 5 peptide on a 100 µmole scale was performed on a Symphony Peptide 30 Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1). Using automated peptide synthesis, the following protected amino acids were sequentially added to Rink Amide MBHA resin: Fmoc-Lys (Boc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbo-OH. The deprotection of the terminal Fmoc group is accomplished using 20% piperidine (Step 2) followed by the coupling of 3-MPA (Step 3). Resin cleavage and product isolation was performed using 86% TFA/5% TIS/5% H$_2$O/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 µm, 21 mm×25 cm column equipped with a Dynamax C$_{18}$, 60 Å, 8 µm guard module, 21 mm×25 cm column and UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 21

Preparation of NAc-Pro-Arg-Lys-Leu-Tyr-Asp-Lys-(Nε-MPA)-NH$_2$.2TFA

Using automated peptide synthesis, the following protected amino acids were sequentially added to Rink Amide MBHA resin: Fmoc-Lys(Aloc)-OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH. Deblocking of the Fmoc group the the N-terminal of the resin-bound amino acid was performed with 20% piperidine in DMF for about 15-20 minutes. Coupling of the acetic acid was performed under conditions similar to amino acid coupling. Final cleavage from the resin was performed using cleavage mixture as described above. The product was isolated by precipitation and purified by preparative HPLC to afford the desired product as a white solid upon lyophilization.

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the 3-maleimidopropionic acid (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H$_2$O (A) and 0.045% TFA in CH$_3$CN (B)) over 180 min at 9.5 mL/min using a Phenomenex Luna 10µ phenyl-hexyl, 21 mm×25 cm column and UV detector (Varian Dynamax UVD II) at λ214 and 254 nm.

Example 22

Preparation of (MPA-AEEA)-Pro-Arg-Lys-Leu-Tyr-Asp-NH$_2$.2TFA

Solid phase peptide synthesis of the modified Kringle 5 peptide on a 100 μmole scale was performed on a Symphony Peptide Synthesizer using Fmoc protected Rink Amide MBHA resin, Fmoc protected amino acids, O-benzotriazol-1-yl-N, N, N',N'-tetramethyl-uronium hexafluorophosphate (HBTU) in N,N-dimethylformamide (DMF) solution and activation with N-methyl morpholine (NMM), and piperidine deprotection of Fmoc groups (Step 1).

Using automated peptide synthesis, the following protected amino acids were sequentially added to Rink Amide MBHA resin: Fmoc-Lys(Boc)-OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH (Step 1). The deprotection of the terminal Fmoc group is accomplished using 20% piperidine (Step 2) followed by the coupling of Fmoc-AEEA. Deprotection of the resulting Fmoc-AEEA-peptide with piperidine 20% in DMF allow for the subsequent addition of the 3-MPA (Step 3). Resin cleavage and product isolation was performed using 86% TFA/5% TIS/5% H$_2$O/2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 μm, 21 mm×25 cm column equipped with a Dynamax C$_{18}$, 60 Å, 8 μm guard module, 21 mm×25 cm column an+d UV detector (Varian Dynamax UVD II) at λ214 and 254 nm. The product had >95% purity as determined by RP-HPLC mass spectrometry using a Hewlett Packard LCMS-1100 series spectrometer equipped with a diode array detector and using electro-spray ionization.

Example 23

Preparation of (MPA)-Pro-Arg-Lys-Leu-Tyr-Asp-NH$_2$.2TFA

Solid phase peptide synthesis of the modified Kringle 5 peptide on a 100 μmole scale was performed on a Symphony Peptide Synthesizer using Fmoc protected Rink Amide MBHA resin, Fmoc protected amino acids, O-benzotriazol-1-yl-N, N, N', N'-tetramethyl-uronium hexafluorophosphate (HBTU) in N,N-dimethylformamide (DMF) solution and activation with N-methyl morpholine (NMM), and piperidine deprotection of Fmoc groups (Step 1). Using automated peptide synthesis, the following protected amino acids were sequentially added to Rink Amide MBHA resin: Fmoc-Lys(Boc)-OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH. The deprotection of the terminal Fmoc group is accomplished using 20% piperidine (Step 2) followed by the coupling of 3-MPA (Step 3). Resin cleavage and product isolation was performed using 86% TFA/5% TIS/5% H$_2$O/ 2% thioanisole and 2% phenol, followed by precipitation by dry-ice cold Et$_2$O (Step 4). The product was purified by preparative reverse phase HPLC using a Varian (Rainin) preparative binary HPLC system using a Dynamax C$_{18}$, 60 Å, 8 μm, 21 mm×25 cm column equipped with a Dynamax C$_{18}$, 60 Å, 8 μm guard module, 21 mm×25 cm column and UV detector (Varian Dynamax UVD 11) at λ214 and 254 nm. The product had >95% purity as determined by RP-HPLC mass spectrometry using a Hewlett Packard LCMS-1100 series spectrometer equipped with a diode array detector and using electro-spray ionization.

Example 24

Preparation of NAc-Pro-Arg-Lys-Leu-Tyr-Asp-Tyr-Lys-(Nε-AEEA-MPA)-NH$_2$.2TFA

Using automated peptide synthesis, the following protected amino acids were sequentially added to Rink Amide MBHA resin: Fmoc-Lys(Aloc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH (Step 1). Deblocking of the Fmoc group at the N-terminal of the resin-bound amino acid was performed with 20% piperidine in DMF for about 15-20 minutes. Coupling of the acetic acid was performed under conditions similar to amino acid coupling. The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition of the AEEA (aminoethoxyethoxyacetic acid) group and of the 3-maleimidopropionic acid (MPA) (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% 30 TFA in H$_2$O (A) and 0.045% TFA in CH$_3$CN (B)) over 180 min at 9.5 mL/min using a Phenomenex Luna 10μ phenylhexyl, 21 mm×25 cm column and UV detector (Varian Dynamax UVD II) at λ214 and 254 nm.

Example 25

Preparation of NAc-Pro-Arg-Lys-Leu-Tyr-Asp-Tyr-Lys-(Nε-AEEA$_n$-MPA)-NH$_2$.2TFA Using automated peptide synthesis, the following protected amino acids were sequentially added to Rink Amide MBHA resin: Fmoc-Lys(Aloc)-OH, Fmoc-Tyr(tBu)OH, Fmoc-Asp(OtBu)-OH, Fmoc-Tyr(tBu)OH, Fmoc-Leu-OH, Fmoc-Lys(Boc)-OH, Fmoc-Arg(Pbf)-OH, Fmoc-Pro-OH (Step 1). Deblocking of the Fmoc group at the N-terminal of the resin-bound amino acid was performed with 20% piperidine in DMF for about 15-20 minutes. Coupling of the acetic acid was performed under conditions similar to amino acid coupling.

The selective deprotection of the Lys(Aloc) group was performed manually and accomplished by treating the resin with a solution of 3 eq of Pd(PPh$_3$)$_4$ dissolved in 5 mL of CHCl$_3$:NMM:HOAc (18:1:0.5) for 2 h (Step 2). The resin was then washed with CHCl$_3$ (6×5 mL), 20% HOAc in DCM (6×5 mL), DCM (6×5 mL), and DMF (6×5 mL). The synthesis was then re-automated for the addition The synthesis was then re-automated for the addition of n AEEA (aminoethoxyethoxyacetic acid) groups and of the 3-maleimidopropionic acid (MPA) (Step 3). Resin cleavage and product isolation was performed using 85% TFA/5% TIS/5% thioanisole and 5% phenol, followed by precipitation by dry-ice cold Et$_2$O (Step 4). The product was purified by preparative reverse phase HPLC using a Varian (Rainin) preparative binary HPLC system: gradient elution of 30-55% B (0.045% TFA in H₂O (A) and 0.045% TFA in CH₃CN (B)) over 180 min at 9.5 mL/min using a Phenomenex Luna 10μ phenyl-hexyl, 21 mm×25 cm column and UV detector (Varian Dynamax UVD II) at λ214 and 254 nm.

Example 26

Peptide Stability Assay

A peptide stability assay was performed. (MPA)-Pro-Arg-Lys-Leu-Tyr-Asp-Lys-NH₂. 2TFA was synthesized as described above and was identified MPA-K5. The non-modified counterpart peptide Pro-Arg-Lys-Leu-Tyr-Asp-Lys-NH₂ was also synthesized as described above without the addition of 3-MPA and identified as K5.

K5 (MW=1260.18, 918.12 freebase) was prepared as a 100 mM stock solution in water. MPA-K5 (MW=1411.17, 1069.11 freebase) was prepared as a 100 mM stock solution in water. Human Serum Albumin (HSA) was obtained as a 25% solution (ca 250 mg/ml, 3.75 mM) as Albutein® available from Alpha Therapeutic. Human plasma was obtained from Golden West Biologicals.

a. Stability of K5 in Human Plasma

K5 was prepared as a 1 μM solution and dissolved in 25% human serum albumin. The mixture was then incubated at 37° C. in the presence of human plasma to final concentration of 160 mM K5. Aliquots of 100 μl were withdrawn from the plasma at 0, 4 hours and 24 hours. The 100 μl aliquots were mixed with 100 μl of blocking solution (5 vol. 5% ZnSO₄/3 vol. Acetonitrile/2 vol. Methanol) in order to precipitate all proteins. The sample was centrifuged for 5 min at 10,000 g and the supernatant containing the peptide was recovered and filtered through a 0.22 μm filter. The presence of free intact K5 peptide was assayed by the HPLC/MS. The HPLC parameters for detection of K5 peptide in serum were as follows.

The HPLC method was as follows: A Vydac C18 250×4.6 mm, 5μ particle size column was utilized. The column temperature was 30° C. with a flow rate of 0.5 ml/min. Mobile Phase A was 0.1% TFA/water. Mobile Phase B was 0.1% TFA/acetonitrite. The injection volume was 10 μl.

The gradient was as follows:

| Time (Minutes) | % A | % B |
|---|---|---|
| 0 | 95 | 5 |
| 20 | 70 | 30 |
| 25 | 10 | 90 |
| 30 | 10 | 90 |
| 35 | 95 | 5 |
| 45 | 95 | 5 |

The proteins were detected at 214, 254 and 334 nm. For mass spectral analysis, the ionization mode was API-electrospray (positive mode) at an M/Z range of 300 to 2000. The gain was 3.0, fragmentor 120 v, threshold 20, stepsize 0.1. The gas temp was 350° C. and the dying gas volume was 10.0 l/min. The Neb pressure was 24 psi and the Vcap was 3500V. The HPLC method was as follows: A Vydac C18 250×4.6 mm, 5μ particle size column was utilized. The column temperature was 30° C. with a flow rate of 0.5 ml/min. Mobile Phase A was 0.1% TFA/water. Mobile Phase B was 0.1% TFA/acetonitrite.

The gradient was as follows:

| Time (Minutes) | % A | % B |
|---|---|---|
| 0 | 95 | 5 |
| 20 | 70 | 30 |
| 25 | 10 | 90 |
| 30 | 10 | 90 |
| 35 | 95 | 5 |
| 45 | 95 | 5 |

The proteins were detected at 214, 254 and 334 nm. For mass spectral analysis, the ionization mode was API-electrospray (positive mode) at an M/Z range of 300 to 2000. The gain was 3.0, fragmentor 120 v, threshold 20, stepsize 0.1. The gas temp was 350° C. and the drying gas volume was 10.0 l/min. The Neb pressure was 24 psi and the Vcap was 3500V.

| Time | % K5 peptide in plasma |
|---|---|
| 0 hrs. | 100% |
| 4 hrs | 9% |
| 24 hrs | 0% |

After only 4 hours incubation in plasma only 9% of the original K5 peptide remained. The results demonstrate that unmodified K5 peptide is unstable in serum likely as a result of protease activity.

b. Stability of MPA-K5-HSA Conjugate in Plasma

MPA-K5 (modified K5 peptide) was incubated with 25% HSA for 2 hours at room temperature. The MPA-K5-HSA conjugate was then incubated at 37° in the presence of human plasma at a final concentration of 160 μm. After the specific incubation period (0, 4 and 24 hours) an aliquot of 100 μl was withdrawn and filtered through a 0.22 μm filter. The presence of intact conjugate was assayed by HPLC-MS.

The column was an Aquapore RP-300, 250×4.6 mm, 7μ particle size. The column temperature was 50° C. The mobile phase A was 0.1% TFA/water. The mobile phase B was 0.1% TFA/acetonitrile. The injection volume was 1 μl. The gradient was as follows:

| Time (minutes) | % A | % B | Flow (ml/min) |
|---|---|---|---|
| 0 | 66 | 34 | 0.700 |
| 1 | 66 | 34 | 0.700 |
| 25 | 58.8 | 41.2 | 0.700 |
| 30 | 50 | 50 | 0.70 |
| 35 | 5 | 95 | 1.00 |
| 41 | 5 | 95 | 1.00 |
| 45 | 66 | 34 | 1.00 |
| 46 | 66 | 34 | 0.70 |

The peptide was detected at 214 mm for quantification. For mass spectral analysis of the peptide, the ionization mode was API-electrospray at 1280 to 1500 m/z range, gain 1.0, fragmentor 125V, threshold 100, stepsize 0.40. The gas temperature was 350° C. the drying gas was 13.0 l/min. The pressure was 60 psi and the Vcap was 6000V. The results are presented below.

Approximately 33% of circulating albumin in the bloodstream is mercaptalbumin (SH-albumin) which is not blocked by endogenous sulfhydryl compounds such as cysteine or glutathione and is therefore available for reaction with maleimido groups. The remaining 66% of the circulating albumin is capped or blocked by sulfhydryl compounds. The HPLC MS assay permits the identification of capped-HSA, SH-albumin and K5-MPA-albumin. The MPA covalently bonds to the free thiol on the albumin. The stability of the three forms of albumin in plasma is presented below.

| Time | % capped HSA | % SH-Albumin | % K5-MPA-HSA |
|---|---|---|---|
| 0 hrs. | 61.3 | 16.6 | 22.1 |
| 4 hrs. | 64.6 | 16.05 | 19.35 |
| 24 hrs. | 63 | 16.8 | 20.2 |

The percentage of the three forms of human serum albumin remained relatively constant throughout the 24 assay period. In particular, the percentage of K5-MPA-HSA remained relatively constant throughout the 24 hour plasma assay. These results are in dramatic contrast to the results obtained with unmodified K5 which decreased to 9% of the original amount of K5 in only 4 hours in plasma. The results demonstrate that, in contrast to K5 which is quite unstable in plasma, K5-MPA-HSA is quite stable from peptidase activity in plasma.

Example 27

Endothelial Cell Migration Assay

The activity of modified anti-angiogenic peptides may be determined with an endothelial cell migration assay. The endothelial cell migration assay may be performed as described by Polyerini, P. J. et al., Methods Enzymol, 198: 440-450 (1991), which is hereby incorporated herein by reference. Briefly, bovine capillary (adrenal) endothelial cells (BCE, which may be obtained from Judah Folkman, Harvard University Medical School) are starved overnight in DMEM containing 0.1% bovine serum albumin (BSA). Cells are then harvested with trypsin and resuspended in DMEM with 0.1% BSA at a concentration of $1.5 \times 10^6$ cells/mL. Cells are added to the bottom of a 48-well modified Boyden chamber (for example from Nucleopore Corporation, Cabin John, Md.).

The chamber is assembled and inverted, and cells are allowed to attach for 2 hours at 37° C. to polycarbonate chemotaxis membranes (5 μm pore size) that is soaked in 0.1% gelatin overnight and dried. The chamber is then reinverted and test substances are added to the wells of the upper chamber (to a total volume of 50 μl); the apparatus is then incubated for 4 hours at 37° C. Membranes are recovered, fixed and stained (DiffQuick, Fisher Scientific, Pittsburgh, Pa.) and the number of cells that have migrated to the upper chamber per 10 high power fields are counted. Background migration to DMEM+0.1% BSA may be subtracted and the data reported as the number of cells migrated per 10 high power fields (400×) or when results from multiple experiments are combined, as the percent inhibition of migration compared to a positive control.

Example 28

Preparation of HSA-Kringle 5 Conjugates

Modified kringle 5 peptides are dissolved in distilled water to a final concentration of 100 mM. For the conjugation reaction, one volume of 100 mM modified kringle 5 peptide is added to 99 volumes of 25% HSA (Albutein®, 25% solution, Alpha Therapeutic inc.) to get 1 mM modified K5: 3.75 mM HSA conjugates. The mixture is allowed to incubate at room temperature for 2 hours. The presence of the conjugate and the absence of unreacted modified K5 peptide are determined by HPLC coupled with mass spectrometry.

Example 29

Effect of Modified Kringle 5 peptides on Endothelial Cell Proliferation In Vitro The biological activity of free and HSA-conjugated Kringle 5 peptides may be determined in vitro using an endothelial cell proliferation assay. Bovine aortic endothelial cells are plated at a density of 2500 cells per well in a 96-well plate in Dulbecco's Modified Eagle medium (DMEM, Gibco) containing 10% heat inactivated calf serum. The cells were allowed to adhere for 24 hours, at 37° C. in a 5% $CO_2$ incubator. The medium is then replaced with fresh DMEM (without serum) containing varying concentrations of inhibitor (free K5 peptide and HSA-Kringle 5 peptides). After 30 minutes at 37° C., bFGF (basic fibroblast growth factor) may then be added to a final concentration of 1 ng/mL to stimulate growth. After 72 hours, the cell number may be measured using the colorimetric substrate WST-1 (Boehringer Mannheim) to determine the effect of modified K5 peptides on endothelial cell proliferation in vitro.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A conjugate formed by a method comprising covalently coupling a modified kringle 5 peptide with human serum albumin, wherein the modified kringle 5 peptide comprises a kringle 5 peptide and a maleimido group coupled to the kringle 5 peptide, optionally via a linking group;
   wherein the kringle 5 peptide is a peptide fragment of amino acid residues 443 to 546 of SEQ ID NO: 1, of between 4 and 104 amino acids, and optionally having an amino acid substitution at $Cys^{523}$;
   wherein the maleimido group and optional linking group is optionally coupled to the kringle 5 peptide by one or more additional amino acids;
   wherein the kringle 5 peptide is optionally coupled to an N-terminal protecting group;
   wherein the kringle 5 peptide has an α-C-terminal carboxy, an α-C-terminal carboxamide, or an α-C-terminal alkylcarboxamide;
   wherein said maleimido group reacts with a thiol group of $Cys^{34}$ of said human serum albumin to form a conjugate that has a 1:1 loading of said kringle 5 peptide to said human serum albumin.

2. The conjugate of claim 1, wherein the kringle 5 peptide is selected from the group consisting of SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

3. The conjugate of claim 1, wherein the kringle 5 peptide is selected from the group consisting of SEQ ID NO:10, SEQ ID NO:11, SEQ ID NO:12, SEQ ID NO:13, SEQ ID NO:14, SEQ ID NO:15 and SEQ ID NO:16.

4. The conjugate of claim 1, wherein the kringle 5 peptide comprises NAc-Pro-Arg-Lys-Leu-Tyr-Asp-Lys-NH$_2$ (SEQ ID NO:17); NAc-Arg-Lys-Leu-Tyr-Asp-Tyr-Lys-NH$_2$ (SEQ ID NO:18); NAc-Tyr-Thr-Thr-Asn-Pro-Arg-Lys-Leu-Tyr-Asp-Tyr-Lys-NH$_2$ (SEQ ID NO:19); NAc-Arg-Asn-Pro-Asp-Gly-Asp-Val-Gly-Gly-Pro-Trp-Ala-Tyr-Thr-Thr-Asn-Pro-Arg-Lys-Leu-Tyr-Asp-Tyr-Lys-NH$_2$ (SEQ ID NO:20); or NAc-Arg-Asn-Pro-Asp-Gly-Asp-Val-Gly-Gly-Pro-Trp-Lys-NH$_2$ (SEQ ID NO:21).

5. The conjugate of claim 1, wherein the modified kringle 5 peptide is selected from the group consisting of NAc-Pro-Arg-Lys-Leu-Tyr-Asp-Tyr-Lys-(Nε-MPA)-NH$_2$ (SEQ ID NO:22); (MPA-AEEA)-Pro-Arg-Lys-Leu-Tyr-Asp-Tyr-NH$_2$ (SEQ ID NO:23); (MPA)- Pro-Arg-Lys-Leu-Tyr-Asp-Tyr- NH$_2$ (SEQ ID NO :24); NAc-Tyr-Thr-Thr-Asn-Pro-Arg-Lys-Leu-Tyr-Asp-Tyr-Lys-(Nϵ-MPA)-NH$_2$ (SEQ ID NO:25); (MPA-AEEA)-Tyr-Thr-Thr-Asn-Pro- Arg-Lys-Leu-Tyr-Asp-Tyr-NH$_2$ (SEQ ID NO:26); (MPA)-Tyr-Thr-Thr-Asn-Pro-Arg-Lys-Leu- Tyr-Asp-Tyr-NH$_2$ (SEQ ID NO:27); NAc-Arg-Asn-Pro-Asp-Gly-Asp-Val-Gly-Gly-Pro-Trp- Ala-Tyr-Thr-Thr-Asn-Pro-Arg-Lys-Leu-Tyr-Asp-Tyr-Lys-(NϵMPA)-NH$_2$ (SEQ ID NO:28); (MPA-AEEA)-Arg-Asn-Pro-Asp-Gly-Asp-Val-Gly-Gly-Pro-Trp-Ala-Tyr-Thr-Thr-Asn-Pro- Arg-Lys-Leu-Tyr-Asp-Tyr-NH$_2$ (SEQ ID NO:29); (MPA)-Arg-Asn-Pro-Asp-Gly-Asp-Val-Gly- Gly-Pro-Trp-Ala-Tyr-Thr-Thr-Asn-Pro-Arg-Lys-Leu-Tyr-Asp-Tyr-NH$_2$ (SEQ ID NO:30); NAc-Arg-Asn-Pro-Asp-Gly-Asp-Val-Gly-Gly-Pro-Trp-Lys-(NϵMPA)-NH$_2$ (SEQ ID NO:31);(MPA-AEEA)-Arg-Asn-Pro-Asp-Gly-Asp-Val-Gly-Gly-Pro-Trp-NH$_2$ (SEQ ID NO:32); (MPA)-Arg- Asn-Pro-Asp-Gly-Asp-Val-Gly-Gly-Pro-Trp-NH$_2$ (SEQ ID NO:33); NAc-Arg-Lys-Leu-Tyr- Asp-Tyr-Lys-(Nϵ-MPA)-NH$_2$ (SEQ ID NO:34); (MPA-AEEA)-Arg-Lys-Leu-Tyr-Asp-Tyr- NH$_2$ (SEQ ID NO:35); (MPA)-Arg-Lys-Leu-Tyr-Asp-Tyr-NH$_2$ (SEQ ID NO:36); NAc-Pro-Arg-Lys- Leu-Tyr-Asp-Lys-(Nϵ-MPA)-NH$_2$ (SEQ ID NO:37); (MPA-AEEA)-Pro-Arg-Lys-Leu-Tyr-Asp- NH$_2$ (SEQ ID NO:38); (MPA)-Pro-Arg-Lys-Leu-Tyr-Asp-NH2 (SEQ ID NO:39); NAc-Pro-Arg- Lys-Leu-Tyr-Asp-Tyr-Lys-(Nϵ-AEEA-MPA)-NH$_2$ (SEQ ID NO:40); and NAc-Pro-Arg-Lys- Leu-Tyr-Asp-Tyr-Lys-(Nϵ-AEEA$_n$-MPA)-NH$_2$ (SEQ ID NO:41).

6. A composition comprising the conjugate of claim 1 in association with a physiologically acceptable medium.

7. The conjugate of claim 2, wherein the kringle 5 peptide is SEQ ID NO: 8.

8. The conjugate of claim 2, wherein the kringle 5 peptide is SEQ ID NO: 9.

9. The conjugate of claim 3, wherein the kringle 5 peptide is SEQ ID NO: 15.

10. The conjugate of claim 5, wherein the modified kringle 5 peptide is (MPA-AEEA)-Tyr-Thr-Thr-Asn-Pro-Arg-Lys-Leu-Tyr-Asp-Tyr-NH$_2$ (SEQ ID NO:26).

11. The conjugate of claim 5, wherein the modified kringle 5 peptide is (MPA)-Tyr-Thr-Thr-Asn-Pro-Arg-Lys-Leu-Tyr-Asp-Tyr-NH$_2$ (SEQ ID NO:27).

12. The conjugate of claim 5, wherein the modified kringle 5 peptide is NAc- Tyr-Thr-Thr-Asn-Pro-Arg-Lys-Leu-Tyr-Asp-Tyr-Lys-(Nϵ-MPA)-NH$_2$ (SEQ ID NO:25).

13. The conjugate of claim 5, wherein the modified kringle 5 peptide is (MPA-AEEA)-Arg-Asn-Pro-Asp-Gly-Asp-Val-Gly-Gly-Pro-Trp-Ala-Tyr-Thr-Thr-Asn-Pro- Arg-Lys-Leu-Tyr-Asp-Tyr-NH$_2$ (SEQ ID NO:29).

14. The conjugate of claim 5, wherein the modified kringle 5 peptide is (MPA)-Arg-Asn-Pro-Asp-Gly-Asp-Val-Gly-Gly-Pro-Trp-Ala-Tyr-Thr-Thr-Asn-Pro-Arg-Lys- Leu-Tyr-Asp-Tyr-NH$_2$ (SEQ ID NO:30).

15. The conjugate of claim 5, wherein the modified kringle 5 peptide is (MPA-AEEA)-Pro-Arg-Lys-Leu-Tyr-Asp-Tyr-NH$_2$ (SEQ ID NO:23).

16. The conjugate of claim 5, wherein the modified kringle 5 peptide is (MPA)-Pro-Arg-Lys-Leu-Tyr-Asp-Tyr-NH$_2$ (SEQ ID NO:24).

17. The conjugate of claim 5, wherein the modified kringle 5 peptide is NAc- Pro-Arg-Lys-Leu-Tyr-Asp-Lys-(Nϵ-MPA)-NH$_2$ (SEQ ID NO:37).

18. The conjugate of claim 5, wherein the modified kringle 5 peptide is NAc-Pro-Arg-Lys-Leu-Tyr-Asp-Tyr-Lys-(Nϵ-MPA)-NH$_2$ (SEQ ID NO:22).

* * * * *

UNITED STATES PATENT AND TRADEMARK OFFICE
CERTIFICATE OF CORRECTION

| | | |
|---|---|---|
| PATENT NO. | : 7,741,286 B2 | Page 1 of 1 |
| APPLICATION NO. | : 11/350703 | |
| DATED | : June 22, 2010 | |
| INVENTOR(S) | : Dominique P. Bridon et al. | |

It is certified that error appears in the above-identified patent and that said Letters Patent is hereby corrected as shown below:

On the Title page, Item (63), second line, "May 15, 2000" should read --May 17, 2000--.

Col. 1, line 8, "May 15, 2000" should read --May 17, 2000--.

Signed and Sealed this
Thirteenth Day of September, 2011

David J. Kappos
*Director of the United States Patent and Trademark Office*